US011116980B2

(12) United States Patent
Nelson et al.

(10) Patent No.: US 11,116,980 B2
(45) Date of Patent: Sep. 14, 2021

(54) COMPLEX VARIATION OF ELECTRICAL STIMULATION THERAPY PARAMETERS

(71) Applicant: Medtronic, Inc., Minneapolis, MN (US)

(72) Inventors: Dwight E. Nelson, Shoreview, MN (US); Thaddeus S. Brink, St. Paul, MN (US); Lance Zirpel, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 371 days.

(21) Appl. No.: 15/946,971

(22) Filed: Apr. 6, 2018

(65) Prior Publication Data

US 2018/0289965 A1    Oct. 11, 2018

Related U.S. Application Data

(60) Provisional application No. 62/482,737, filed on Apr. 7, 2017.

(51) Int. Cl.
*A61N 1/36* (2006.01)

(52) U.S. Cl.
CPC ..... *A61N 1/36189* (2013.01); *A61N 1/36007* (2013.01); *A61N 1/36064* (2013.01);
(Continued)

(58) Field of Classification Search
CPC ............ A61N 1/36135; A61N 1/36007; A61N 1/36067; A61N 1/36071; A61N 1/36085;
(Continued)

(56) References Cited

U.S. PATENT DOCUMENTS

| 4,338,945 A | 7/1982 | Kosugi et al. |
| 4,541,432 A | 9/1985 | Molina-Negro et al. |

(Continued)

FOREIGN PATENT DOCUMENTS

| CN | 107050645 A | 8/2017 |
| EP | 2396072 B1 | 3/2013 |

(Continued)

OTHER PUBLICATIONS

Mathworks, "rand", https://www.mathworks.com/help/matlab/ref/rand.html, before version 2006, viewed on Jan. 16, 2021.*

(Continued)

*Primary Examiner* — Carl H Layno
*Assistant Examiner* — James Moss
(74) *Attorney, Agent, or Firm* — Shumaker & Sieffert, P.A.

(57) ABSTRACT

Techniques for delivering electrical stimulation therapy comprising a complex variation to at least one electrical stimulation parameter are described. In one example, processing circuitry of an implantable medical device (IMD) identifies a plurality of electrical stimulation parameters for at least one pulse train of electrical stimulation. The processing circuitry defines a complex variation to at least one electrical stimulation parameter of the plurality of electrical stimulation parameters. The processing circuitry modifies the at least one pulse train of electrical stimulation by introducing the complex variation to the electrical stimulation parameter function and controls a stimulation generator of the IMD to generate, as modified, the at least one pulse train of electrical stimulation.

24 Claims, 14 Drawing Sheets

(52) U.S. Cl.
CPC ..... *A61N 1/36067* (2013.01); *A61N 1/36071* (2013.01); *A61N 1/36085* (2013.01); *A61N 1/36107* (2013.01); *A61N 1/36125* (2013.01); *A61N 1/36135* (2013.01); *A61N 1/36153* (2013.01); *A61N 1/36157* (2013.01); *A61N 1/36171* (2013.01); *A61N 1/36175* (2013.01); *A61N 1/36178* (2013.01); *A61N 1/3615* (2013.01)

(58) Field of Classification Search
CPC ............ A61N 1/36064; A61N 1/36107; A61N 1/36178; A61N 1/36153; A61N 1/36157; A61N 1/36171; A61N 1/36175; A61N 1/36189; A61N 1/36125; A61N 1/3615
See application file for complete search history.

(56) References Cited

U.S. PATENT DOCUMENTS

| | | | |
|---|---|---|---|
| 5,603,726 A | 2/1997 | Schulman et al. | |
| 5,800,465 A | 9/1998 | Thompson et al. | |
| 6,289,247 B1 | 9/2001 | Faltys et al. | |
| 6,314,325 B1 | 11/2001 | Fitz | |
| 6,421,566 B1 | 7/2002 | Holsheimer | |
| 6,505,078 B1 | 1/2003 | King et al. | |
| 6,675,046 B2 | 1/2004 | Holsheimer | |
| 6,850,802 B2 | 2/2005 | Holsheimer | |
| 6,988,006 B2 | 1/2006 | King et al. | |
| 7,050,856 B2 | 5/2006 | Stypulkowski | |
| 7,263,402 B2 | 8/2007 | Thacker et al. | |
| 7,333,858 B2 | 2/2008 | Killian et al. | |
| 7,571,001 B2 | 8/2009 | Thacker et al. | |
| 7,577,480 B2 | 8/2009 | Zeijlemaker | |
| 7,657,318 B2 | 2/2010 | King et al. | |
| 7,689,289 B2 | 3/2010 | King | |
| 7,742,810 B2 | 6/2010 | Moffitt et al. | |
| 8,359,103 B2 | 1/2013 | Alataris et al. | |
| 8,504,150 B2 | 8/2013 | Skelton | |
| 8,620,441 B2 | 12/2013 | Greenberg et al. | |
| 8,694,108 B2 | 4/2014 | Alataris et al. | |
| 8,708,934 B2 | 4/2014 | Skelton et al. | |
| 8,712,533 B2 | 4/2014 | Alataris et al. | |
| 8,712,534 B2 | 4/2014 | Wei | |
| 8,788,048 B2 | 7/2014 | Bennett et al. | |
| 8,923,988 B2 | 12/2014 | Bradley | |
| 9,002,460 B2 | 4/2015 | Parker | |
| 9,138,582 B2 | 9/2015 | Doan et al. | |
| 9,155,892 B2 | 10/2015 | Parker et al. | |
| 9,186,510 B2 | 11/2015 | Gliner et al. | |
| 9,339,655 B2 | 5/2016 | Carbunaru | |
| 9,358,391 B2 | 6/2016 | Zhu et al. | |
| 9,381,356 B2 | 7/2016 | Parker et al. | |
| 9,381,360 B2 | 7/2016 | Hershey | |
| 9,386,934 B2 | 7/2016 | Parker et al. | |
| 9,604,058 B2 | 3/2017 | Moffitt | |
| 9,707,394 B2 | 7/2017 | Bennett, II et al. | |
| 9,789,306 B2 | 10/2017 | Sabourin et al. | |
| 9,808,627 B2 | 11/2017 | Gliner et al. | |
| 9,827,422 B2 | 11/2017 | Zhu | |
| 9,950,165 B2 | 4/2018 | Howard | |
| 10,118,036 B2 | 11/2018 | Zhu | |
| 10,118,038 B2 | 11/2018 | De Ridder | |
| 10,207,109 B2 | 2/2019 | Zhu et al. | |
| 10,213,605 B2 | 2/2019 | Grill et al. | |
| 10,315,031 B2 | 6/2019 | Brink et al. | |
| 2002/0127144 A1 | 9/2002 | Mehta | |
| 2004/0267333 A1 | 12/2004 | Kronberg | |
| 2005/0070987 A1 | 3/2005 | Erickson | |
| 2007/0255364 A1 | 1/2007 | Gerber et al. | |
| 2007/0067004 A1 | 3/2007 | Boveja et al. | |
| 2007/0100388 A1* | 5/2007 | Gerber ............... A61N 1/36007 607/41 |
| 2007/0244522 A1 | 10/2007 | Overstreet | |
| 2008/0269833 A1 | 10/2008 | Scott et al. | |
| 2009/0036945 A1 | 2/2009 | Chancellor et al. | |
| 2009/0131993 A1 | 5/2009 | Rousso et al. | |
| 2009/0222053 A1 | 9/2009 | Gaunt et al. | |
| 2010/0121416 A1 | 5/2010 | Lee | |
| 2010/0152807 A1 | 6/2010 | Grill et al. | |
| 2010/0222686 A1 | 9/2010 | Fisher et al. | |
| 2010/0228079 A1 | 9/2010 | Forsell | |
| 2011/0054570 A1 | 3/2011 | Lane | |
| 2011/0071589 A1 | 3/2011 | Starkebaum et al. | |
| 2011/0093041 A1 | 4/2011 | Straka et al. | |
| 2011/0125223 A1 | 5/2011 | Carbunaru et al. | |
| 2011/0282412 A1 | 11/2011 | Glukhovsky et al. | |
| 2012/0101326 A1 | 4/2012 | Simon et al. | |
| 2012/0130444 A1 | 5/2012 | Wei et al. | |
| 2012/0155188 A1 | 6/2012 | Buettner et al. | |
| 2012/0197336 A1* | 8/2012 | Su ...................... A61N 1/36178 607/41 |
| 2012/0197337 A1 | 8/2012 | Su et al. | |
| 2012/0277621 A1* | 11/2012 | Gerber ................. A61B 5/4836 600/554 |
| 2012/0296389 A1 | 11/2012 | Fang et al. | |
| 2013/0110194 A1 | 5/2013 | Wei | |
| 2013/0208390 A1 | 8/2013 | Singh et al. | |
| 2013/0231715 A1* | 9/2013 | Grill, Jr. ............. A61N 1/36082 607/59 |
| 2013/0238066 A1 | 9/2013 | Boggs, II et al. | |
| 2013/0268021 A1 | 10/2013 | Moffitt | |
| 2013/0289664 A1 | 10/2013 | Johanek | |
| 2013/0293025 A1 | 11/2013 | Xu et al. | |
| 2014/0005753 A1 | 1/2014 | Carbunaru | |
| 2014/0025146 A1 | 1/2014 | Alataris et al. | |
| 2014/0031896 A1 | 1/2014 | Alataris et al. | |
| 2014/0031905 A1 | 1/2014 | Irazoqui et al. | |
| 2014/0074186 A1 | 3/2014 | Faltys et al. | |
| 2014/0074189 A1 | 3/2014 | Moffitt | |
| 2014/0142656 A1 | 5/2014 | Alataris et al. | |
| 2014/0142673 A1 | 5/2014 | Alataris et al. | |
| 2014/0243924 A1* | 8/2014 | Zhu ..................... A61N 1/36146 607/46 |
| 2014/0296936 A1 | 10/2014 | Alataris et al. | |
| 2014/0371813 A1 | 12/2014 | King et al. | |
| 2014/0379043 A1 | 12/2014 | Howard | |
| 2015/0127062 A1 | 5/2015 | Holley | |
| 2015/0179177 A1 | 6/2015 | Nagao | |
| 2015/0217117 A1* | 8/2015 | Hershey ............. A61N 1/36178 607/59 |
| 2016/0030741 A1 | 2/2016 | Wei et al. | |
| 2016/0136420 A1 | 5/2016 | Brink et al. | |
| 2016/0346546 A1* | 12/2016 | Zhu ..................... A61N 1/36071 |
| 2017/0028021 A1 | 2/2017 | Howard | |
| 2017/0209695 A1 | 7/2017 | Solomon | |
| 2017/0312523 A1 | 11/2017 | Bennett et al. | |
| 2018/0154144 A1 | 6/2018 | Brink et al. | |
| 2018/0289965 A1 | 10/2018 | Nelson et al. | |
| 2019/0001139 A1 | 1/2019 | Mishra et al. | |
| 2019/0038901 A1 | 2/2019 | Zhu | |
| 2020/0346018 A1 | 11/2020 | Grill et al. | |

FOREIGN PATENT DOCUMENTS

| | | |
|---|---|---|
| EP | 2813262 B1 | 10/2015 |
| WO | 2002009808 A1 | 2/2002 |
| WO | 2010058178 A1 | 5/2010 |
| WO | 2010123704 A1 | 10/2010 |
| WO | 2011156286 A1 | 12/2011 |
| WO | 2015179177 A1 | 11/2015 |
| WO | 2015179281 A1 | 11/2015 |
| WO | 2016127130 A1 | 8/2016 |
| WO | 2016191055 A1 | 12/2016 |
| WO | 2017106503 A1 | 6/2017 |
| WO | 2017214638 A1 | 12/2017 |

OTHER PUBLICATIONS

Warman et al., "Modeling the Effects of Electric Fields on Nerve Fibers: Determination of Excitation Thresholds," IEEE Transac-

(56) References Cited

OTHER PUBLICATIONS tions on Biomedical Engineering, vol. 39, No. 12, Dec. 1992, pp. 1244-1254.
Zhang et al., "Influence of Inter-Stimulus Interval of Spinal Cord Stimulation in Patients with Disorders of Consciousness: A Preliminary Functional Near-Infrared Spectroscopy Study," NeuroImage: Clinical, vol. 17, Sep. 23, 2017, 9 pp.
Thrasher et al., "Reducing Muscle Fatigue Due to Functional Electrical Stimulation Using Random Modulation of Stimulation Parameters," Artificial Organs, vol. 29, No. 6, Feb. 2005, pp. 453-458.
Slavin, "Spinal Stimulation for Pain: Future Applications," Neurotherapeutics, Apr. 3, 2014, pp. 535-541.
Redman et al., "Monosynaptic Stochastic Stimulation of Cat Spinal Motoneurons. II. Frequency Transfer Characteristics of Tonically Discharging Motoneurons," Journal of Neurophysiology, vol. 31, No. 4, , Jul. 1968, pp. 499-508.
Pinter et al., "Epidural Electrical Stimulation of Posterior Structures of the Human Lumboscral Cord: 3. Control of Spasticity," Spinal Cord, vol. 38, No. 9, Sep. 2000, pp. 524-531.
Redman et al., "Monosynaptic Stochastic Stimulation of Cat Soinal Motoneurons. I. Response of Motoneurons to Sustained Stimulation," vol. 31, No. 4, Jul. 1968, pp. 485-498.
Si et al., "Spinal Cord Stimulation Frequency Influences the Hemodynamic Response in Patients with Disorders of Consciousness," Neuroscience Bulletin, vol. 34, No. 4, Aug. 2018, pp. 659-667.
Martinez et al., "Stochastic Resonance in the Motor System: Effects of Noise on the Monosynaptic Reflex Pathway of the Cat Spinal Cord," Journal of Neurophysiology, vol. 97, No. 6, Apr. 11, 2007, pp. 4007-4016.
Manjarrez et al., "Internal Stochastic Resonance in the Coherence Between Spinal and Cortical Neoronal Ensembles in the Cat," Neuroscience Letters, vol. 326, Feb. 2002, pp. 93-96.
Chang et al., "Stochastic Versus Deterministic Variability in Simple Neuronal Circuits: 1. Monosynaptic Spinal Cord Reflexes," Biophysics Journal, vol. 67, Aug. 1994, pp. 671-683.
Dimitrijevic et al., "Habituation: Effects of Regular and Stochastic Stimulation," Journal of Neurology, Neurosurgery, and Psychiatry, vol. 35, No. 2, Apr. 1972, pp. 234-242.
Manjarrez et al., "Stochastic Resonance within the Somatosensory System: Effects of Noise on Evoked Field Potentials Elicited by Tactile Stimuli," The Journal of Neuroscience, vol. 23, No. 6, Mar. 15, 2003, pp. 1997-2001.
De Ridder et al., "Fundamentals of Burst Stimulation of the Spinal Cord and Brain," Chapter 14, Neuromodulation, Second Edition, Available online Jan. 12, 2018, pp. 147-160.
Aksoz et al. "Effect of Stochastic Modulation of Inter-Pulse Interval During Stimulated Isokinetic Leg Extension," European Journal of Translational Myology, vol. 26, No. 3.
Bloodworth et al., "Comparison of Stochastic vs.Conventional Transcutaneous Electrical Stimulation for PainModulation in Patients withElectromyographically Documented Radiculopathy," American Journal of Physical and Medical Rehabilitation, vol. 83, No. 8, Aug. 2004, pp. 584-591.
Irazoqui et al., "System for Wireless Recording and Stimulating of Bioelectric Events," DARPA N66001-11-1-4029, Dec. 12, 2017, 6 pp.
Woock et al., Activation and Inhibition of the Micturition Reflex by Penile Afferents in the Cat, American journal of physiology. Regulatory, Integrative and Comparative Physiology, vol. 294, Apr. 23, 2008, pp. R1880-R1889.
Seburn et al., "Miniature Wireless and Batteryless Device for Longitudinal Recording and Stimulating of Bioelectric Events in Small Animals," 45th Annual Meeting of the Society for Neuroscience, Oct. 17-21, 2015, 1 pp.
U.S. Appl. No. 62/348,405, by Irazoqui et al., filed Jun. 10, 2016.
International Preliminary Report on Patentability from International Application No. PCT/US2018/026536, dated Oct. 17, 2019, 8 pp.

"St. Jude's Prodigy Neurostimulator with Burst Technology," Medgadget, Mar. 20, 2014, 4 pp.
Abejon et al., "Back pain coverage with spinal cord stimulation: A different treatment for each patient," International Neuromodulation Society. Jun. 10, 2015; 567, Abstract Only, 1 pp.
Abeloos, et al., "High density stimulation as an alternative to uncomfortable cervical tonic spinal cord stimulation: case report," International Neuromodulation Society 12th World Congress, Jun. 11-15, 2015, Abstract Only, 1 pp.
Bhadra et al., "High frequency electrical conduction block of the pudendal nerve," Journal of Neural Eng., IOP Publishing Ltd, published Jun. 3, 2006, 14 pp.
Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.
Breel, et al., "High Density Stimulation: A novel programming paradigm for the treatment of chronic pain," International Neuromodulation Society (INS) 12th World Congress; Jun. 9, 2015, Abstract Only, 1 pp.
Cuellar MD et al., "Effect of high-frequency alternating current on spinal afferent nociceptive transmission," Neuromodulation: Technology at the Neural Interface, vol. 16, No. 4, Jul.-Aug. 2013, pp. 318-327.
Cui et al., "Spinal cord stimulation attenuates augmented dorsal horn release of excitatory amino acids in mononeuropathy via a GABAergic mechanism," Pain 73, Oct. 1997, pp. 87-95.
Cui et al., "Effect of spinal cord stimulation on tactile hypersensitivity in mononeuropathic rats is potentiated by simultaneous GABA(B) and adenosine receptor activation," Neuroscience Letters 247: Apr. 1998; pp. 183-186.
De Ridder et al., "Burst spinal cord stimulation for limb and back pain," World neurosurgery, vol. 80, No. 5, Nov. 2013, pp. 642-649 e641.
De Ridder et al., "Burst spinal cord stimulation: toward paresthesia-free pain suppression," Neurosurgery, vol. 66, No. 5, May 2010, pp. 986-990.
Downey, "Asynchronous Neuromuscular Electrical Stimulation," University of Florida, 2015, accessed on Jul. 18, 2016, 107 pp.
Duyyendak, MD, et al., "High density stimulation: a novel programming paradigm for the treatment of chronic back and leg pain," Abstracts, International Neuromodulation Society 12th World Congress: Jun. 11-15, 2015, 1 pp.
Gao et al., "Effects of spinal cord stimulation with "standard clinical" and higher frequencies on peripheral blood flow in rats," Brain Res. Feb. 8, 2010; 1313: pp. 53-61.
Grider, et al., "High Frequency (1000 Hz) Stimulation Using Commercially Available Implantable Pulse Generator," North American Neuromodulation Society. Dec. 2013, Abstract Only, 2 pp.
Guan et al., "Spinal cord stimulation-induced analgesia: electrical stimulation of dorsal column and dorsal roots attenuates dorsal horn neuronal excitability in neuropathic rats," Anesthesiology, vol. 113, No. 6, Dec. 2010, pp. 1392-1405.
Guan et al., "Spinal Cord Stimulation: Neurophysiological and Neurochemical Mechanisms of Action" Curr Pain Headache Rep DOI 10,1007s11916-014-0260-4, Mar. 2012, pp. 217-225.
Holsheimer, "Computer modelling of spinal cord stimulation and its contribution to therapeutic efficacy," Spinal Cord, vol. 36, Aug. 1998, pp. 531-540.
Hunt et a., "The molecular dynamics of pain control," National Reviews, Neuroscience, vol. 2, No. 2, Feb. 2001, 83-91.
Kemler et al., "Spinal cord stimulation in patients with chronic reflex sympathetic dystrophy," New England Journal of Medicine, vol. 343, No. 9, Aug. 31, 2000, pp. 618-624.
Kilgore et al., "Reversible Nerve Conduction Block Using Kilohertz Frequency Alternating Current," Neuromodulation. Aug. 2013, pp. 242-255.
Kumar et al., "Spinal cord stimulation versus conventional medical management for neuropathic pain: a multicentre randomised controlled trial in patients with failed back surgery syndrome," Pain Jul. 2007; 132(1-2): 179-188.

(56) References Cited

OTHER PUBLICATIONS

Likar et al., "High density spinal cord stimulation: a multi-center experience," Abstracts, International Neuromodulation Society 12th World Congress; Jun. 11-15, 2015, 1 pp.

Maeda et al., "Increased c-fos immunoreactivity in the spinal cord and brain following spinal cord stimulation is frequency-dependent," Brain Res. Mar. 9, 2009; 1259: pp. 40-50.

Maeda et al., "Low frequencies, but not high frequencies of bi-polar spinal cord stimulation reduce cutaneous and muscle hyperalgesia induced by nerve injury," Pain, vol. 138, No. 1, Feb. 2008, pp. 143-152.

North et al., "Spinal cord stimulation versus repeated lumbosacral spine surgery for chronic pain: a randomized, controlled trial," Neurosurgery, vol. 56, No. 1, Jan. 2005, 98-106; discussion 106-107.

North et al., "Clinical outcomes of 1 kHz subperception spinal cord stimulation (SCS): Results of a prospective randomized controlled crossover trial," Abstracts, International Neuromodulation Society, Jun. 2015, 1 pp.

Ranck Jr., et al., "Which elements are excited in electrical stimulation of mammalian central nervous system: a review," Brain Research, vol. 98, No. 3, Nov. 21, 1975, pp. 417-440.

Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato et al., "Spinal cord stimulation reduces hypersensitivity through activation of opioid receptors in a frequency-dependent manner," European Journal of Pain, Apr. 17, 2012, pp. 551-561.

Schu et al., "A prospective, randomised, double-blind, placebo-controlled study to examine the effectiveness of burst spinal cord stimulation patterns for the treatment of failed back surgery syndrome," Neuromodulation, vol. 17, No. 5, Apr. 2014, pp. 443-450.

Shechter et al., "Conventional and kilohertz-frequency spinal cord stimulation produces intensity- and frequency-dependent inhibition of mechnical hypersensitivity in a rat model of neuropathic pain," Anesthesiology, vol. 119, No. 2, Aug. 2013, pp. 422-432.

Sluka et al., "High-Frequency, But Not Low-Frequency, Transcutaneous Electrical Nerve Stimulation Reduces Aspartate and Glutamate Release in the Spinal Cord Dorsal Horn," Journal of Neurochemistry, vol. 95, No. 6 Oct. 17, 2005, pp. 1794-1801.

Smith et al., "Successful use of high-frequency spinal cord stimulation following traditional treatment failure," Stereotactic and Functional Neurosurgery, vol. 93, No. 3, Apr. 2015, pp. 190-193.

Song et al., "Efficacy of kilohertz-frequency and conventional spinal cord stimulation in rat models of different pain conditions," Neuromodulation, vol. 17, No. 3, Jan. 2014, pp. 226-234.

Sweet et al., "High Frequency vs. Burst Stimulation Patterns for Dorsal Column Stimulation: The Importance of Charge," American Association of Neurological Surgeons, Abstract, Apr. 4, 2014, 2 pp.

Wille et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.

Youn et al., "The Effect of High Frequency Stimulation on Sensory Thresholds in Chronic Pain Patients," North American Neuromodulation Society. 2014, 1 pp. (Applicant points out in accordance with MPEP 609.04(a) that the 2014 year of publication is sufficiently earlier than the effective U.S. filing date of the present application, and any foreign priority date that the particular month of publication is not in issue.).

International Search Report and Written Opinion of International Application No. PCT/US2018/026536, dated Jul. 4, 2018, 14 pp.

Hubscher et al., "Convergence and cross talk in urogenital neural circuitries," Journal of Neurophysiology, The American Physiological Society, Jul. 31, 2013, 9 pp.

Maggi, et al., "Effect of urethane anesthesia on the micturition reflex in capsaicin-treated rats." Journal of the Autonomic Nervous System, Jan. 1990, 30(3): 247-251.

Snellings et al., "Effects of stimulation site and stimulation parameters on bladder inhibition by electrical nerve stimulation," BJU International, Aug. 9, 2011, 8 pp.

Walter et al., "Inhibiting the Hyperreflexic Bladder with Electrical Stimulation in a Spinal Animal Model," Neurourology and Urodynamics, Oct. 19, 1992, 12 pp.

Woock et al., "Activation and inhibition of the micturition reflex by penile afferents in the cat," American Journal Physiology, Apr. 23, 2008, 11 pp.

Response to Communication Pursuant to Rules 161(1) and 162 EPC dated Nov. 19, 2019, from counterpart European Application No. 18720885.5, filed May 19, 2020, 17 pp.

Communication pursuant to Article 94(3) EPC from counterpart European Application No. 18720885.5, dated Dec. 2, 2020, 6 pp.

Communication pursuant to Rules 161(1) and 162 EPC from counterpart European Application No. 18720885.5, dated Nov. 14, 2019, 3 pp.

* cited by examiner

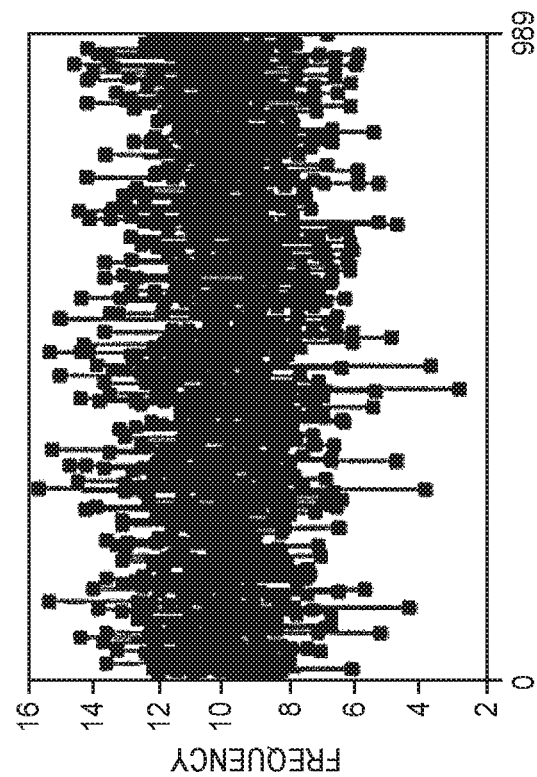
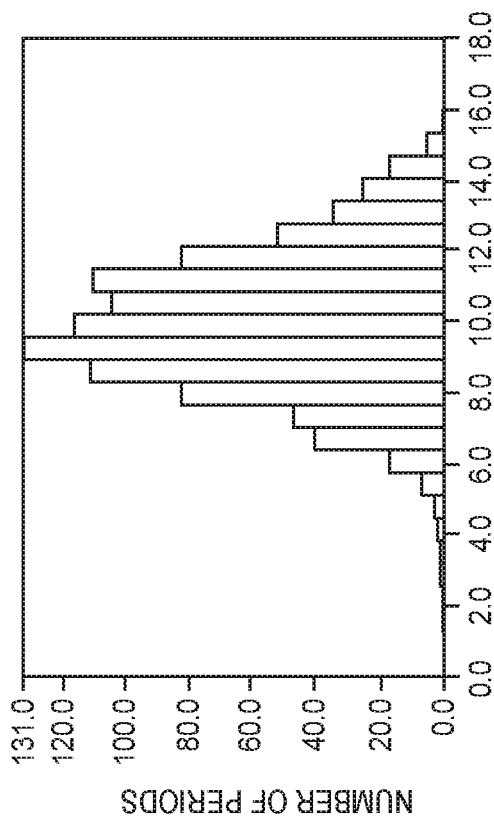
FIG. 8A
FIG. 8B

COMPLEX VARIATION OF ELECTRICAL STIMULATION THERAPY PARAMETERS

This application claims the benefit of U.S. Provisional Patent Application No. 62/482,737 filed on Apr. 7, 2017, the entire content of which is incorporated by reference herein.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, epilepsy, urinary or fecal incontinence, sexual dysfunction, obesity, gastroparesis, visceral disorders, cognitive disorders, and movement disorders. A medical device may deliver electrical stimulation therapy via one or more electrodes located proximate to target locations associated with the brain, the spinal cord, pelvic nerves, peripheral nerves, or the gastrointestinal tract of a patient. Electrodes may be deployed, for example, on implantable leads and/or implantable device housings. Electrical stimulation may be used in different therapeutic applications, such as deep brain stimulation (DBS), spinal cord stimulation (SC S), pelvic floor stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a recharge interval, a pulse width, a pulse frequency, and/or an inter-stimulation interval as stimulation parameters. One or more parameters of the electrical stimulation therapy, such as electrode combination, electrode polarity, amplitude, pulse width, pulse rate, and duty cycle define the electrical stimulation therapy to be delivered to the patient.

SUMMARY

In general, the disclosure describes techniques for delivering, to a patient, electrical stimulation therapy that includes complex variation of one or more parameters of the stimulation. In one example, a clinician configures a medical device to deliver, to a patient, electrical stimulation therapy defined by one or more electrical stimulation parameters. For example, the clinician may set an upper limit for one or more values of the one or more electrical stimulation parameters based on sensed responses by the patient. Processing circuitry of the medical device may modify the one or more electrical stimulation parameters by introducing complex variation to the one or more electrical stimulation parameters and deliver electrical stimulation therapy defined by the modified electrical stimulation parameters via implantable electrodes to one or more tissue sites of the patient to reduce, alleviate or otherwise address one or more symptoms of the patient.

In some examples, the complex variation is a periodic or stochastic function. The stochastic function may be an actual stochastic function or approximate a stochastic function (e.g., a pseudo-random function that exhibits characteristics of randomness but is deterministic rather than random). In some examples, the stochastic function is a uniform probabilistic distribution. In other examples, the stochastic function is a non-uniform probabilistic distribution.

In one example, this disclosure describes a method for providing neuromodulation therapy to a patient using an implantable medical device (IMD), the method comprising: identifying, with processing circuitry of the IMD, a plurality of electrical stimulation parameters for at least one pulse train of electrical stimulation; defining, with the processing circuitry of the IMD, a complex variation to at least one electrical stimulation parameter of the plurality of electrical stimulation parameters to reduce a pelvic symptom of the patient; modifying, with the processing circuitry of the IMD, the at least one pulse train of electrical stimulation by introducing the complex variation to the at least one electrical stimulation parameter; and generating, as modified and with a stimulation generator of the IMD, the at least one pulse train of electrical stimulation.

In another example, this disclosure describes an implantable medical device (IMD) configured to provide neuromodulation therapy to a patient comprising: a stimulation generator configured to generate at least one pulse train of electrical stimulation for delivery to the patient; and processing circuitry configured to: identify a plurality of electrical stimulation parameters for the at least one pulse train of electrical stimulation; define a complex variation to at least one electrical stimulation parameter of the plurality of electrical stimulation parameters to reduce a pelvic symptom of the patient; modify the at least one pulse train of electrical stimulation by introducing the complex variation to the at least one electrical stimulation parameter; and control the stimulation generator to generate, as modified, the at least one pulse train of electrical stimulation.

In another example, this disclosure describes an implantable medical device configured to provide neuromodulation therapy to a patient comprising: means for identifying a plurality of electrical stimulation parameters for at least one pulse train of electrical stimulation; means for defining a complex variation to at least one electrical stimulation parameter of the plurality of electrical stimulation parameters to reduce a pelvic symptom of the patient; means for modifying the at least one pulse train of electrical stimulation by introducing the complex variation to the at least one electrical stimulation parameter; and means for generating, as modified, the at least one pulse train of electrical stimulation.

In another example, this disclosure describes a non-transitory, computer-readable medium comprising instructions that, when executed, cause processing circuitry of an implantable medical device (IMD) configured to provide neuromodulation therapy to a patient to: identify a plurality of electrical stimulation parameters for at least one pulse train of electrical stimulation; define a complex variation to at least one electrical stimulation parameter of the plurality of electrical stimulation parameters to reduce a pelvic symptom of the patient; modify the at least one pulse train of electrical stimulation by introducing the complex variation to the at least one electrical stimulation parameter; and control a stimulation generator of the IMD to generate, as modified, the at least one pulse train of electrical stimulation.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 8A-8B are charts illustrating example values for a frequency of electrical stimulation that varies over time based on a stochastic function in accordance with the techniques of the disclosure.

Like reference characters refer to like elements throughout the figures and description.

DETAILED DESCRIPTION

Figure 1:
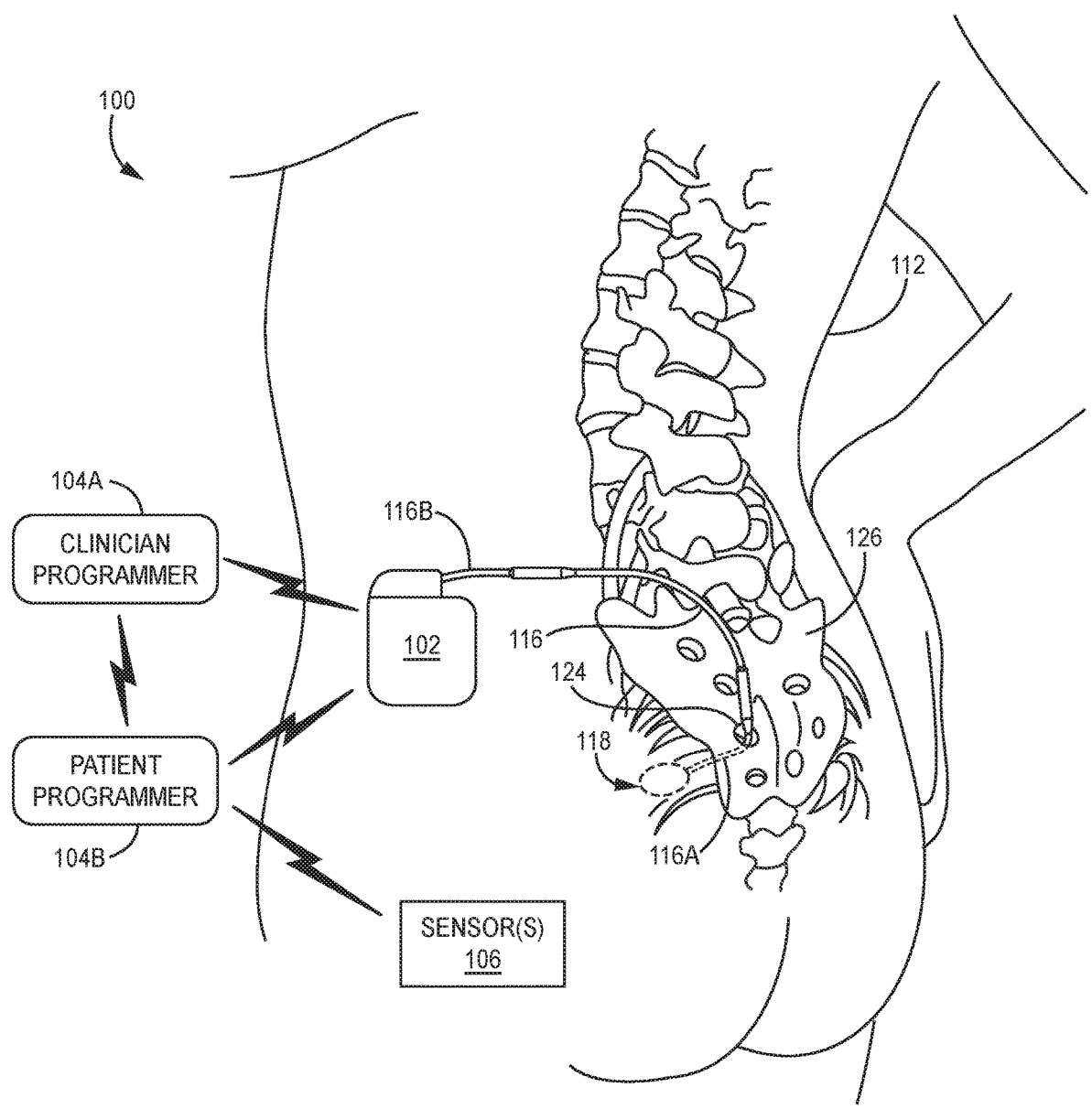
FIG. 1 is a conceptual diagram illustrating an example system that includes a medical device programmer and an implantable medical device (IMD) configured to deliver electrical stimulation therapy including complex variation of at least one electrical stimulation parameter to a patient.

Nervous systems extract, create, and process information through operations within complex and dynamic neural circuits. Neurostimulation inputs to these circuits have been used to treat a number of conditions ranging from brain disorders, visceral disorders, pain, cognitive disorders, movement disorders, and other dysfunctions. Signals that stimulate or perturb these complex neural processing systems may be static or constant, and are most often based on the input easiest to create electronically. More complex and dynamic input signals may have increased capacities to impact both normal and dysfunctional neural circuits. Techniques are disclosed herein for providing temporally complex pulse trains of stimulation delivered to peripheral nervous systems. Such temporally complex pulse trains may have increased impact on animal and human physiology. Potential complex or dynamic patterns can be generated by introducing variations to stimulation parameters during the pulse trains, such as by modulating the frequency or amplitude. Certain embodiments are directed toward introducing complex and dynamic patterns by introducing parameter changes that follow a predetermined pattern, such as ramping the amplitude or frequency in a particular direction. Other predetermined patterns can include introducing a periodic change to the parameter. As non-limiting examples, the periodic change can be in the form of an oscillatory or pulsatile change or defined by a function. These patterns and others can be temporally applied to the baseline electrical stimulation pulse train to generate a electrical stimulation pulse train comprising a complex variation and then delivered to one or several targeted therapy sites. Temporal modulation of these trains may occur independent of physiological signals or may be phase- or time-locked to physiological or environmental markers.

Experimental suggest that sufficiently complex, dynamic patterns of stimulation at a peripheral nerve site of a mammal can provide an improved inhibitory response of neurological tissue. For instance, a stochastic stimulation pattern of amplitudes has been found to produce a bladder quieting response in sheep, which can be beneficial for treatment of conditions such as overactive bladder. The discovery that bladder quieting response to stochastic amplitude stimulation is improved relative to bladder quieting response to constant stimulation with a fixed amplitude and frequency was unexpected and surprising given that on average, a similar amount of energy is delivered to the tissue in both types of stimulation. Without being limited by theory, such greater bladder quieting response may result from a richer or larger information-carrying capacity of the input signal or by activating richer or larger information transmission capacities within targeted nerves. For example, the medical device may deliver such electrical stimulation therapy to a sacral nerve of the patient to reduce one or more symptoms of a pelvic disease or disorder of the patient, such as urinary incontinence or other pelvic symptoms of a patient. Furthermore, such complex patterns of stimulation may have greater efficacy in inhibiting neural activity and/or transmission. Thus, the techniques of the disclosure may have greater efficacy in suppressing pain of the patient over conventional constant stimulation with a fixed amplitude and frequency. Accordingly, as another example, the medical device as described herein may deliver such complex electrical stimulation therapy to a spinal nerve of the patient to suppress pain of the patient, or to a brain of the patient to treat one or more symptoms of a degenerative disease, such as Parkinson's disease.

Accordingly, techniques are disclosed herein for a system that includes a medical device programmer and an implantable medical device (IMD) configured to deliver electrical stimulation therapy by introducing a complex, time-varying component to the electrical stimulation. Consistent with various embodiments, the time varying component that is sufficiently complex to achieve improved neurological inhibiting. One factor in the complexity can be the range over which that the parameter can be adjusted. For instance, the range could be set based upon a percentage of a baseline value for the parameter (e.g., a value between 5% and 80% of a maximum tolerable value, as described below). Another factor can be the period, if any, of the complex pattern. For instance, a deterministic function can be used to generate a pseudorandom set of values that can be generated as needed or stored in a lookup table. The set of values may be repeated once the last value in the set is reached. The size of the set can be a relevant factor in the complexity of the resulting signal. Yet another factor can be the amount of complexity or randomness in the series. There are several metrics that could be used in assessing the complexity or randomness including, but not limited to, the Kolmogorov complexity or determining the number of different frequencies created as can be measured using a frequency analysis of the generated signal (e.g., using a Fast Fourier Transform).

Systems designed to deliver electrical stimulation to a patient according to a constant amplitude and/or frequency over time can be implemented with relatively simple circuitry and control logic. However, electrical stimulation based on a stochastic function as described herein may present random or pseudo-random properties (e.g., properties that approximate a truly random or stochastic function) that have greater efficacy in impacting both normal and dysfunctional excitable tissues of the patient than electrical stimulation delivered according to simple, constant signal waveforms alone. For example, delivery of electrical stimulation, defined based on the stochastic function as described herein, to a sacral nerve of the patient may exhibit increased bladder quieting responses over electrical stimulation having a constant (e.g., fixed) amplitude.

FIG. 1 is a conceptual diagram illustrating an example system that includes a medical device programmer and an implantable medical device (IMD) configured to deliver electrical stimulation therapy including complex variation of at least one electrical stimulation parameter to a patient. In some examples, the electrical stimulation therapy comprises neuromodulation therapy. Electrical stimulation system 100 is configured to deliver electrical stimulation to a target tissue, such as one or more nerves in the pelvic floor, in the example of FIG. 1. In some examples, system 100 may generate stimulation continuously, in response to a sensed signal, according to a predetermined duty cycle or at predetermined times.

In other examples, system 100 may receive input from a user, e.g., patient 112, indicating that patient 112 is attempting to contract one or more pelvic floor muscles and deliver electrical stimulation to a target tissue site proximate a nerve of patient 112 based on the input. For example, the electrical stimulation may be configured to induce or suppress a contraction in the pelvic floor muscles. The targeted nerve can be a nerve that influences the sensory, motor, or autonomic control of the pelvic floor of patient 112, such as a sacral nerve, a pudendal nerve, or a branch of the sacral or pudendal nerves. While the sacral and pudendal nerves are primarily referred to throughout the disclosure, in other examples, therapy system 100, as well as the other systems, can include delivery of stimulation to tissue sites proximate to other nerves in addition to or instead of the sacral or pudendal nerves. Moreover, reference to the sacral and pudendal nerves may include branches of the sacral and pudendal nerves that may also influence the behavior of pelvic floor muscles of patient 112. In further examples, therapy system 100 includes delivery of stimulation to tissue sites proximate to lumbar or thoracic spinal nerves or their branches, such as chain ganglia, sympathetic or parasympathetic ganglia, S1-S5, a dorsal nerve of a clitoris or a penis, an inferior rectal nerve, a peroneal nerve, a sciatic nerve, a tibial nerve, or other nerve targets, such as a spinal cord of patient 112, or portions of the spinal cord, or peripheral targets that may be stimulated using externally targeted therapies.

Although system 100 may deliver electrical stimulation to modulate muscle activity to treat incontinence and/or overactive bladder (e.g., contract or relax a sphincter or inhibit bladder contractions), system 100 may also deliver stimulation configured to treat pain or other symptoms. In some examples, system 100 may be configured to deliver stimulation to nerves that innervate the bladder, the rectum, or sexual organs in order to treat a variety of symptoms. In other examples, system 100 may be configured to provide spinal cord stimulation, peripheral nerve stimulation, occipital nerve stimulation, gastric stimulation, or any other therapy configured to modulate organ or muscle activity and/or treat pain. In yet further examples, system 100 may be configured to deliver deep brain stimulation (DBS) to patient 112 to suppress one or more neurological symptoms of patient 112, such as tremor or rigidity due to Parkinson's disease, seizures associated with epilepsy, or other brain disorders.

In the example of FIG. 1, electrical stimulation system 100 includes implantable medical device (IMD) 102, which is coupled to lead 116, for delivering electrical stimulation to target tissue site 118 of patient 112. The electrical stimulation may be delivered via one or more electrodes carried by lead 116 and/or one or more electrodes carried by a housing of IMD 102. In addition, electrical stimulation system 100 may include clinician programmer 104A and patient programmer 104B (collectively, "programmers 104") for permitting a clinician or patient 112, respectively, to provide user input to control the operation of electrical stimulation system 100 and/or review diagnostic or operational information collected by the system. In some examples, only a single external programmer may be used to communicate with IMD 102.

IMD 102 may provide electrical stimulation therapy to target tissue site 118 of patient 112 by generating a programmable electrical stimulation signal (e.g., in the form of electrical pulses, signals, or waveforms) and delivering the electrical stimulation signal to target tissue site 118 via lead 116. In some examples, IMD 102 is a neurostimulator that provides neuromodulation therapy to patient 112. In some examples, IMD 102 is located proximate a sacral nerve or a pudendal nerve of patient 112. In some examples, lead 116 includes one or more stimulation electrodes, disposed on distal end 116A of lead 116 and implanted proximate to target tissue site 118 such that the electrical stimulation is delivered from IMD 102 to target tissue site 118 via the stimulation electrodes.

In some examples described herein, target tissue site 118 includes at least one of a sacral nerve of patient 112 or a pudendal nerve of patient 112 (or a tissue site proximate the sacral or pudendal nerve, wherein delivery of electrical stimulation to the tissue site captures the nerve). The sacral and pudendal nerves of patient 112 may be involved in inducing a contraction in one or more muscles of the pelvic floor of patient 112. As a result, electrical stimulation of the sacral and/or pudendal nerves of patient 112 may be useful in treating the pelvic floor disorder of patient 112.

In general, the sacral nerves include five sacral nerves that emerge from the sacrum. In some examples, the sacral vertebrae (S1-S5) may be used to number the sacral nerves. The sacral nerves contribute to the sacral plexus (a network of intersecting nerves that innervates the posterior thigh, part of the lower leg, the foot, and part of the pelvis) and the coccygeal plexus (a network of intersecting nerves near the coccyx bone, e.g., the tailbone, that innervates the skin of the coccyx bone and around the anus). In general, the pudendal nerve is a somatic nerve in the pelvic region, which is a large branch of the sacral plexus. The pudendal nerve innervates the external genitalia, the urinary sphincters, and the anal sphincters.

As illustrated in FIG. 1, distal end 116A of lead 116 is implanted proximate to target tissue site 118. In the example shown in FIG. 1, target tissue site 118 is proximate the S3 sacral nerve of patient 112. In this example, in order to implant distal end 116A of lead 116 proximate to the S3 sacral nerve, lead 116 may be introduced into the S3 sacral foramen 124 of sacrum 126 to access the S3 sacral nerve. For some patients, stimulation of the S3 sacral nerve may be effective in treating a pelvic floor disorder of the patient. In other examples, distal end 116A may be implanted proximate to a different target tissue site, such as a target tissue site proximate to a different sacral nerve or a pudendal nerve of patient 112 to treat the pelvic floor disorder of patient 112.

Although FIG. 1 illustrates one lead 116, in some examples, IMD 102 may be coupled to two or more leads, e.g., to facilitate bilateral or multi-lateral stimulation. In some examples, lead 116 may also carry one or more sense electrodes via which IMD 102 can sense one or more physiological parameters (e.g., nerve signals, EMG, and the like) of patient 112, in addition to the one or more stimulation electrodes carried by lead 116. In some examples, lead 116 includes a lead body, and electrodes carried by lead 116, e.g., at proximal end 116B of lead 116, may be electrically coupled to IMD 102 via one or more conductors extending substantially through the lead body between the one or more stimulation electrodes carried by lead 116 and IMD 102.

In the example shown in FIG. 1, lead 116 is cylindrical. One or more electrodes of lead 116 may be ring electrodes, segmented electrodes, or partial ring electrodes. Segmented and partial ring electrodes each extend along an arc less than 360 degrees (e.g., 90-120 degrees) around the outer perimeter of the lead 116. In some examples, segmented electrodes may be useful for targeting different fibers of the same or different nerves to generate different physiological effects. The electrodes of lead 116 may be used for low frequency stimulation (e.g., less than approximately 50 Hertz) to induce or suppress responses in pelvic muscles or nerves of patient 112. In some examples, lead 116 may be, at least in part, paddle-shaped (i.e., a "paddle" lead).

In some examples, one or more of the electrodes of lead 116 may be cuff electrodes that are configured to extend at least partially around a nerve (e.g., extend axially around an outer surface of a nerve). In some cases, delivering stimulation via one or more cuff electrodes and/or segmented electrodes may help achieve a more uniform or directional electrical field or activation field distribution relative to the nerve, which may help reduce discomfort to patient 112 that results from the delivery of electrical stimulation. An electrical field represents the areas of a patient anatomical region that are covered by an electrical field during delivery of electrical stimulation to tissue within patient 112. The electrical field may define the volume of tissue that is affected when the electrodes of lead 116 are activated to deliver stimulation energy. An activation field represents the neurons that will be activated by the electrical field in the neural tissue proximate to the activated electrodes.

A combination of electrodes carried on lead 116 (or multiple leads) may form a bipolar or multipolar combination of one or more cathodes and one or more anodes for delivery of stimulation. Alternatively, one or more electrodes carried on lead 116 may form a unipolar combination with an electrode carried on a housing of IMD 102. For example, one or more cathodes on lead 116 may form an electrode combination with an anode on the housing of IMD 102, or one or more anodes on lead 116 may form an electrode combination with a cathode on the housing IMD 102. As a further alternative, an electrode combination may include one or more anodes and one more cathodes on lead 116 in combination with an anode or cathode on the housing of IMD 116.

The illustrated numbers and configurations of lead 116 and electrodes carried by lead 116 are merely one example. Different configurations, e.g., different quantities and/or positions of leads and electrodes, are possible. For example, in other examples, IMD 102 may be coupled to additional leads or lead segments having one or more electrodes positioned at different locations in the pelvic region of patient 112.

IMD 102 may be surgically implanted in patient 112 at any suitable location within patient 112, such as within in an abdomen of patient 112. In some examples, the implantation site may be a subcutaneous location in the side of the lower abdomen or the side of the lower back or upper buttocks. IMD 102 has a biocompatible outer housing, which may be formed from titanium, stainless steel, a liquid crystal polymer, or the like. In some examples, electrical conductors disposed within the lead body of lead 116 electrically connect electrodes to electrical stimulation delivery circuitry within IMD 102. In other examples, therapy system 100 may include a leadless electrical stimulator, such as a microstimulator (e.g., a capsule shaped microstimulator), where the leadless electrical stimulator delivers electrical stimulation to target tissue site 118, and, in some examples, senses one or more physiological parameters of patient 112, via electrodes on an outer surface of the electrical stimulator housing and without the aid of electrodes of a lead that extends from the electrical stimulator housing.

IMD 102 may deliver electrical stimulation to manage a pelvic symptom or a pelvic dysfunction of patient 112 (e.g., electrical stimulation for a voiding disorder or urinary incontinence). In these examples, IMD 102 may deliver electrical stimulation configured to contract a muscle (e.g., the urinary sphincter) to help suppress or prevent involuntary voiding events in order to manage, e.g., urinary incontinence or fecal incontinence of patient 112. In addition, or alternatively, IMD 102 may deliver electrical stimulation configured to relax a bladder (e.g., inhibit bladder contractions) of patient 112 to help prevent urgency. In other examples, electrical stimulation may be provided to train and/or strengthen pelvic floor muscles. In still further examples, IMD 102 may deliver electrical stimulation configured to control other pelvic symptoms or pelvic dysfunctions, such as over-active bladder (OAB) disease, pelvic pain, sexual dysfunction, and other visceral or pelvic disorders. In still further examples, IMD 102 may promote or support voiding by patients suffering from urinary retention disorder.

In the example illustrated in FIG. 1, system 100 includes clinician programmer 104A and patient programmer 104B. In some examples, one or both programmers 104A and 104B may be wearable communication devices integrated into a key fob or a wrist watch. In other examples, one or both programmers 104A and 104B may be handheld computing devices, such as tablet computers, or computer workstations, or networked computing devices. Programmers 104 may include respective user interfaces that receive input from a user (e.g., a clinician or patient 112, respectively). The user interfaces may include components for interaction with a user, such as a keypad and a display. In some examples, the display may be a liquid crystal display (LCD) or light emitting diode (LED) display and the keypad may take the form of an alphanumeric keypad, or a reduced set of keys associated with particular functions. Programmers 104 can, additionally or alternatively, include a peripheral pointing device, e.g., a mouse, via which a user may interact with the user interface. In some examples, the displays may include a touch screen display, and a user may interact with programmers 104 via the touch screens of the displays. In some examples, the user may also interact with programmers 104 and/or IMD 102 remotely via a networked computing device.

Clinician programmer 104A facilitates interaction of a clinician with one or more components of system 100. In some examples, the clinician, (e.g., physician, technician, surgeon, electrophysiologist, or other clinician) may interact with clinician programmer 104A to communicate with IMD 102. For example, the clinician may retrieve physiological or diagnostic information from IMD 102 via clinician programmer 104A. As another example, the clinician may interact with programmer 104A to program IMD 102, e.g., select values of respective stimulation parameters that define electrical stimulation generated and delivered by IMD 102, or select other operational parameters of IMD 102, etc. As another example, the clinician may use programmer 104A to retrieve information from IMD 102 regarding the performance or integrity of IMD 102 or other components of system 100, such as lead 116 or a power source of IMD 102. In some examples, this information may be presented to the clinician as an alert if a system condition that may affect the efficacy of therapy is detected.

In some examples, a clinician may use clinician programmer 104A to create stimulation programs for electrical stimulation (generated and delivered by IMD 102) of the nerves configured to induce or suppress a contraction in one or more pelvic floor muscles of the patient. The stimulation programs may describe a plurality of different electrical stimulus parameters for delivering electrical stimulus therapy to patient 112. The electrical stimulus parameter may, in some examples, specify the number or time duration of one or more stimulation pulses, the number of times the electrical stimulus is delivered within a particular period of time (e.g., daily), particular times of day at which the electrical stimulus is delivered, and other parameters relating to the delivery of stimulation to patient 112. In some examples, the clinician programmer 104A transmits the stimulation programs and/or the training schedules to IMD 102 for storage in a memory of IMD 102.

Patient programmer 104B facilitates interaction of patient 112 with one or more components of system 100. In some examples, patient 112 may interact with patient programmer 104B to control IMD 102 to deliver electrical stimulation, to select or adjust stimulation programs or parameters, to manually abort the delivery of electrical stimulation by IMD 102, or to inhibit the delivery of electrical stimulation by IMD 102. Patient 112 may, for example, use a keypad or touch screen of programmer 104B to cause IMD 102 to deliver electrical stimulation, e.g., to activate one or more stimulation programs, to initiate one or more training schedules, and the like.

IMD 102, clinician programmer 104A, and patient programmer 104B may communicate via wireless communication using any techniques known in the art. Examples of communication techniques may include, for example, low frequency or radiofrequency (RF) telemetry. In some examples, programmer 104A and/or programmer 104B may include a programming head that may be placed proximate to the body of the patient near the IMD 102 implant site in order to improve the quality or security of communication between IMD 102 and programmers 104. In other examples, programmer 104A and/or programmer 104B may use long distance telemetry to communicate with IMD 102.

According to the techniques of the disclosure, IMD 102 delivers electrical stimulation therapy defined by complex variation of one or more electrical stimulation therapy parameters. In one example, a clinician, via external programmer 104, configures one or more electrical stimulation therapy parameters to define electrical stimulation therapy that IMD 102 delivers to patient 112. For instance, the clinician may configure the one or more electrical stimulation therapy parameters to a baseline level during a clinical or outpatient visit. In some examples, the clinician configures the one or more electrical stimulation therapy parameters based on patient feedback.

IMD 102 modifies the one or more electrical stimulation parameters by introducing complex variation to the one or more electrical stimulation parameters, generates electrical stimulation therapy defined by the modified electrical stimulation parameters, and delivers electrical stimulation therapy defined by the modified electrical stimulation parameters via implantable electrodes. In some examples, the clinician, via external programmer 104, may enable or disable the complex variation of the one or more electrical stimulation parameters.

The electrodes, as in the example of FIG. 1, may be positioned along lead 116 to target tissue site 118 of patient 112 to reduce, alleviate or otherwise address one or more symptoms of patient 112. For example, IMD 102 may deliver such electrical stimulation therapy to a sacral nerve of patient 112 to reduce one or more symptoms of a pelvic disease of patient 112. As another example, IMD 102 may deliver such electrical stimulation therapy to a spinal nerve of patient 112 to suppress pain of patient 112, or to a brain of patient 112 to treat one or more symptoms of a degenerative disease, such as Parkinson's disease.

In some examples, the complex variation comprises variation based on a periodic function or a stochastic function. For example, a stochastic function may be used to define a probabilistic distribution of values. Values of the probabilistic distribution may be used as values of the one or more parameters defining the electrical stimulation. For example, the stochastic function may define a uniform probabilistic distribution of values. A uniform probabilistic distribution is a probabilistic distribution wherein each value within the distribution has an equal chance of occurring. For example, the outcome of a coin toss has a uniform probabilistic distribution in that both heads and tails have an equal chance of occurring.

In other examples, the stochastic function defines a non-uniform probabilistic distribution of values. A non-uniform probabilistic distribution is a probabilistic distribution wherein each value within the distribution does not have an equal chance of occurring. Examples of non-uniform probabilistic distributions include a unimodal Gaussian probabilistic distribution (e.g., a normal probabilistic distribution), a half-normal probabilistic distribution, a multimodal Gaussian probabilistic distribution, a log-normal probabilistic distribution, a binomial probabilistic distribution, a geometric probabilistic distribution, or an exponential probabilistic distribution. In yet further examples, the stochastic function may apply an equation to define the probabilistic distribution of values.

While the techniques of the disclosure are illustrated herein with respect to unimodal Gaussian and half-normal probabilistic distributions, the stochastic function of the techniques described herein may define a variety of different probabilistic distributions. As an illustration, in other examples, the stochastic function defines a discrete probabilistic distribution having finite support. Examples of such a discrete probabilistic distribution having finite support include a Bournoulli probabilistic distribution, a Rademacher probabilistic distribution, a binomial probabilistic distribution, a beta-binomial probabilistic distribution, a degenerate probabilistic distribution, a discrete uniform probabilistic distribution, a hypergeometric probabilistic distribution, a Poisson binomial probabilistic distribution, a Fisher's noncentral hypergeometric probabilistic distribution, a Wallenius's noncentral hypergeometric probabilistic distribution, and a Benford's law probabilistic distribution.

In yet additional examples, the stochastic function may define a discrete probabilistic distribution having infinite support. Examples of such a discrete probabilistic distribution having infinite support include a beta negative binomial probabilistic distribution, a Boltzmann probabilistic distribution, a Gibbs probabilistic distribution, a Maxwell-Boltzmann probabilistic distribution, a Borel probabilistic distribution, a Champernowne probabilistic distribution, an extended negative binomial probabilistic distribution, an extended hypergeometric probabilistic distribution, a generalized log-series probabilistic distribution, a geometric probabilistic distribution, a logarithmic series probabilistic distribution, a negative binomial probabilistic distribution, a compound Poisson probabilistic distribution, a parabolic fractal probabilistic distribution, a Poisson probabilistic distribution, a Conway-Maxwell-Poisson probabilistic distribution, a Zero-truncated Poisson probabilistic distribution, a Polya-Eggenberger probabilistic distribution, a Skellam probabilistic distribution, a skew elliptical probabilistic distribution, a Tule-Simon probabilistic distribution, a zeta probabilistic distribution, a Zipf probabilistic distribution, and a Zipf-Mandelbrot probabilistic distribution.

In yet additional examples, the stochastic function may define a continuous probabilistic distribution supported on a bounded interval. Examples of such a continuous probabilistic distribution supported on a bounded interval include an arcsine probabilistic distribution, a Beta probabilistic distribution, a logit-normal probabilistic distribution, a Dirac delta probabilistic distribution, a continuous uniform probabilistic distribution, a degenerate probabilistic distribution, a rectangular probabilistic distribution, an Irwin-Hall probabilistic distribution, a Bates probabilistic distribution, a Kent probabilistic distribution, a Kumaraswamy probabilistic distribution, a continuous logarithmic probabilistic distribution, a Marchenko-Pastur probabilistic distribution, a PERT probabilistic distribution, a raised cosine probabilistic distribution, a reciprocal probabilistic distribution, a triangular probabilistic distribution, a trapezoidal probabilistic distribution, a truncated normal probabilistic distribution, a U-quadratic probabilistic distribution, a con Mises-Fisher probabilistic distribution, and a Wigner semicircle probabilistic distribution.

In yet additional examples, the stochastic function may define a continuous probabilistic distribution supported on an interval of $2\pi$. Examples of such a continuous probabilistic distribution supported on an interval of $2\pi$ include a von Mises probabilistic distribution, a wrapped normal probabilistic distribution, a wrapped exponential probabilistic distribution, a wrapped Levy probabilistic distribution, a wrapped Cauchy probabilistic distribution, a wrapped Laplace probabilistic distribution, and a Dirac comb probabilistic distribution.

In yet additional examples, the stochastic function may define a continuous probabilistic distribution supported on a semi-infinite interval. Examples of such a continuous probabilistic distribution supported on a semi-infinite interval include a Beta prime probabilistic distribution, a Birnbaum-Saunders probabilistic distribution, a chi probabilistic distribution, a noncentral chi probabilistic distribution, a chi-squared probabilistic distribution, an inverse-chi-squared probabilistic distribution, a noncentral chi-squared probabilistic distribution, a scaled-inverse-chi-squared probabilistic distribution, a Dagum probabilistic distribution, an exponential probabilistic distribution, an exponential-logarithmic probabilistic distribution, an F probabilistic distribution, a noncentral F probabilistic distribution, a Fisher's Z probabilistic distribution, a folded probabilistic distribution, a Frechet probabilistic distribution, a Gamma probabilistic distribution, an Erlang probabilistic distribution, an inverse gamma probabilistic distribution, a generalized gamma probabilistic distribution, a generalized Pareto probabilistic distribution, a Gamma/Gompertz probabilistic distribution, a Gompertz probabilistic distribution, a half-normal probabilistic distribution, Hotelling's T-squared probabilistic distribution, an inverse Gaussian probabilistic distribution, a Levy probabilistic distribution, a log-Cauchy probabilistic distribution, a log-Laplace probabilistic distribution, a log-logistic probabilistic distribution, a log-normal probabilistic distribution, a Lomax probabilistic distribution, a Mittag-Leffler probabilistic distribution, a Nakagama probabilistic distribution, a Pareto probabilistic distribution, a Pearson Type-III probabilistic distribution, a Phase-type probabilistic distribution, a phased bi-exponential probabilistic distribution, a phased bi-Weibull probabilistic distribution, a Rayleigh probabilistic distribution, a Rayleigh mixture probabilistic distribution, a Rice probabilistic distribution, a shifted Gompertz probabilistic distribution, a Type-2 Gumbel probabilistic distribution, a Weibull probabilistic distribution, and a Rosin Rammler probabilistic distribution.

In yet additional examples, the stochastic function may define a continuous probabilistic distribution supported on an infinite interval. Examples of such a continuous probabilistic distribution supported on an infinite interval include a Behrens-Fisher probabilistic distribution, a Cauchy probabilistic distribution, a Chernoff s probabilistic distribution, an exponentially-modified Gaussian probabilistic distribution, a Fisher-Tippett probabilistic distribution, a Fisher's Z probabilistic distribution, a skewed generalized T probabilistic distribution, a generalized logistic probabilistic distribution, a generalized normal probabilistic distribution, a geometric stable probabilistic distribution, a Gumbel probabilistic distribution, a Holtsmark probabilistic distribution, a hyperbolic probabilistic distribution, a hyperbolic secant probabilistic distribution, a Johnson SU probabilistic distribution, a Landau probabilistic distribution, a Laplace probabilistic distribution, a Levy skew alpha-stable probabilistic distribution, a Linnik probabilistic distribution, a logistic probabilistic distribution, a map-Airy probabilistic distribution, a normal probabilistic distribution, a normal-exponential-gamma probabilistic distribution, a normal-inverse Gaussian probabilistic distribution, a Pearson Type-IV probabilistic distribution, a skew-normal probabilistic distribution, a Student's T probabilistic distribution, a noncentral T probabilistic distribution, a skew-T probabilistic distribution, a Type-1 Gumbel probabilistic distribution, a Tracy-Widom probabilistic distribution, a Voigt probabilistic distribution, a Gaussian minus exponential probabilistic distribution, and a Chen probabilistic distribution.

In yet additional examples, the stochastic function may define a continuous probabilistic distribution supported on a variable interval. Examples of such a continuous probabilistic distribution supported on a variable interval include a generalized extreme value probabilistic distribution, a generalized Pareto probabilistic distribution, a Tukey lambda probabilistic distribution, and a Wakeby probabilistic distribution.

In some examples, the stochastic function defines a probabilistic distribution of values that are a series of random values, while in other examples, the stochastic function defines a probabilistic distribution of values that are a series of pseudo-random values (e.g., an approximated random or stochastic function). Such a series of pseudo-random values exhibit or approximate true statistical randomness, but are deterministic and not truly random. The series of pseudo-random values may be computationally easier for IMD 102 to generate, while being substantially comparable to a series of truly random values.

In some examples, IMD 102 uses the stochastic function to determine a series of values that vary over time for one or more parameters that define the electrical stimulation delivered to the patient. In some examples, IMD 102 uses the stochastic function to determine a series of values for one or more of a pulse voltage amplitude or a pulse current amplitude of the electrical stimulation, a recharge interval of the electrical stimulation, a pulse width of the electrical stimulation, a duty cycle of the electrical stimulation, a pulse frequency, and/or an inter-stimulation interval of the electrical stimulation. Thus, IMD 102 may use the stochastic function to impart a degree of randomness to one or more parameters of the electrical stimulation so as to deliver more effective stimulation to, or stimulate a greater cross section of, nerve fibers and tissue of the patient than is possible with electrical stimulation that does not vary over time based on the stochastic function. For example, variation of one or more parameter values of the electrical stimulation over time, such as the amplitude value, may stimulate different fascicles and fibers of a larger nerve. Over time, the variation of parameter values may result in increased efficacy over systems that deliver electrical stimulation of a continuous amplitude value. Further, the response of nerve fibers to the electrical stimulation may vary depending on the distance and orientation of the nerve fibers to the electrical stimulation. In other words, the nerve fiber response may be location-dependent (e.g., depend on whether the nerve fibers receive near-field or far-field electrical stimulation). Such variation of the one or more parameter values of the electrical stimulation over time may deliver near-field or far-field electrical stimulation to the nerve fibers, evoking varying responses from the nerve fibers over time.

In some examples, a clinician determines a maximum tolerable value for the one or more parameters defining the electrical stimulation, such as one of a maximum pulse voltage amplitude or pulse current amplitude. In other words, the clinician determines a maximum value for the one or more parameters defining the electrical stimulation that does not cause undesirable sensations, e.g., such as paresthesia or pain, perceptible by patient 112. The maximum tolerable value is a subjective, measured value that is unique to each lead placement in each subject. In some examples, the maximum tolerable value is a maximum tolerable current amplitude determined to be within a range from 0.1 milliamps and 25 milliamps.

In some examples, the stochastic function defines a unimodal half-normal probabilistic distribution having a mean or median centered at or below the maximum tolerable value for the one or more parameters defining the electrical stimulation. In other examples, the stochastic function defines a multimodal Gaussian probabilistic distribution having one or more modes less than or equal to the maximum tolerable value for the one or more parameters defining the electrical stimulation. In these examples, the maximum tolerable value acts as a maximum upper bound for the values of the one or more parameters defining the electrical stimulation. In other words, the stochastic function defines, according to the probabilistic distribution, a series of values for the one or more parameters that define the electrical stimulation delivered to patient 112. Further, each of the series of values are less than or equal to the maximum tolerable value for the one or more parameters defining the electrical stimulation. In some examples, the values of the one or more parameters defining the electrical stimulation are selected from a range of about 5% to about 80% of the maximum tolerable value.

In some examples, the electrical stimulation has a frequency selected from a range of 1 Hz to 50,000 Hz. In other examples, the electrical stimulation has a frequency selected from a range of 5 Hz to 5,000 Hz. In another example, the electrical stimulation has a frequency selected from a range of 0.15 Hertz to 40 Hertz. In other examples, the electrical stimulation has a frequency selected from a range of 1 Hertz to 50 Kilohertz. In other examples, the electrical stimulation has a frequency selected from a range of 10 Hertz to 150 Hertz. In another example, the electrical stimulation has a frequency selected from a range of 2 Hertz to 20 Hertz.

In some examples, the electrical stimulation has a current amplitude selected from a range of 0 milliamps to 40 milliamps. In other examples, the electrical stimulation has a current amplitude selected from a range of 0 milliamps to 25 milliamps. In other examples, the electrical stimulation has a current amplitude selected from a range of 0.1 milliamps to 25 milliamps. In other examples, the electrical stimulation has a current amplitude selected from a range of 0 milliamps to 7.8 milliamps. In some examples, the electrical stimulation has a voltage amplitude selected from a range of 50 millivolts to 10 volts. In another example, the electrical stimulation has a voltage amplitude selected from a range of 500 millivolts to 5 volts.

In some examples, IMD 102 delivers a post-stimulation recharge pulse immediately after delivering a pulse of electrical stimulation. Such a recharge pulse is typically performed to clear out any residual charge that is left over from the stimulation energy, e.g., a residual polarization voltage or after-potential that occurs following the delivery of a pulse of electrical stimulation. For example, such residual charge may occur in a tip capacitor of IMD 102, at one or more leads 116, or in the surrounding tissue. The post-stimulation recharge pulse is typically opposite in amplitude (e.g., a negative amplitude) with respect to the electrical stimulation pulse. For example, the electrical stimulation therapy includes electrical stimulation pulses comprising a positive amplitude interleaved with recharge pulses comprising a negative amplitude. The post-stimulation recharge pulse typically ends well before the next electrical stimulation pulse within an electrical stimulation period to allow for other functionality to take place, for example, R-wave sensing to confirm capture.

In an example of the above, the one or more parameters of an example system include a pulse current amplitude and the stochastic function defines a unimodal half-normal probabilistic distribution having a mean centered on the maximum tolerable value. In this example, the maximum tolerable value is 7.8 milliamps. The stochastic function defines values for the pulse current amplitude of the electrical stimulation, wherein the values for the pulse current amplitude of the electrical stimulation are distributed along the unimodal half-normal probabilistic distribution and are equal to or less than 7.8 milliamps. In some examples, the values for the pulse current amplitude include 0 milliamp values (e.g., wherein no stimulation is delivered), while in other examples values for the pulse current amplitude do not include 0 milliamp values.

In an example of the above, the one or more parameters of an example system include a pulse current amplitude and the stochastic function defines a unimodal Gaussian or half-normal probabilistic distribution having a mean centered on the maximum tolerable value. In this example, the maximum tolerable value is approximately 1.0 milliamp. The stochastic function defines values for the pulse current amplitude of the electrical stimulation, wherein the values for the pulse current amplitude of the electrical stimulation are distributed along the unimodal half-normal probabilistic distribution and are equal to or less than approximately 1.0 milliamps. Further, the stochastic function has a coefficient of variation of 0.2. In some examples, the values for the pulse current amplitude include 0 milliamp values (e.g., wherein no stimulation is delivered), while in other examples values for the pulse current amplitude do not include 0 milliamp values.

As another example of the above, the one or more parameters of an example system include a pulse voltage amplitude and the stochastic function defines a multimodal Gaussian probabilistic distribution having a plurality of modes less than the maximum tolerable value. In this example, the maximum tolerable value is 10 volts. The stochastic function defines values for the pulse current amplitude of the electrical stimulation, wherein the values for the pulse current amplitude of the electrical stimulation are distributed along the multimodal Gaussian probabilistic distribution probabilistic distribution and are equal to or greater than approximately 50 millivolts and less than or equal to approximately 10 volts.

In a further example, wherein the one or more parameters include a pulse voltage amplitude, the maximum tolerable value is 5 volts. The stochastic function defines values for the pulse current amplitude of the electrical stimulation, wherein the values for the pulse current amplitude of the electrical stimulation are distributed along the multimodal Gaussian probabilistic distribution probabilistic distribution and are equal to or greater than approximately 500 millivolts and less than or equal to approximately 5 volts.

In an example of the above, the one or more parameters of an example system include a pulse current amplitude and a pulse frequency. In this example, a first stochastic function defines a unimodal half-normal probabilistic distribution having a mean less than the maximum tolerable value. In this example, the maximum tolerable value is determined to be within a range of 0.1 milliamps to 25 milliamps. The first stochastic function defines values for the pulse current amplitude of the electrical stimulation, wherein the values for the pulse current amplitude of the electrical stimulation are distributed along the unimodal half-normal probabilistic distribution and are equal to or less than maximum tolerable value. Further, a second stochastic function defines a unimodal normal probabilistic distribution having a mean centered on 10 Hertz, a lower bound of 0.15 Hertz, and an upper bound of 40 Hertz. The second stochastic function defines values for the pulse frequency of the electrical stimulation, wherein the values for the pulse frequency of the electrical stimulation are distributed along the unimodal normal probabilistic distribution and are between the lower bound of 0.15 Hertz and the upper bound of 40 Hertz. In some examples, the values for the pulse current amplitude include 0 milliamp values, while in other examples values for the pulse current amplitude do not include 0 milliamp values.

In further examples wherein the one or more parameters include two or more parameters, the two or more parameters may co-variate (e.g., have correlated variation). In such an example, the system may vary over time both the pulse current amplitude and the pulse frequency, such that electrical stimulation having a low-amplitude also has a low-frequency, while electrical stimulation having a high-amplitude also has a high-frequency. Alternatively, the system may vary over time both the pulse current amplitude and the pulse frequency, such that electrical stimulation having a low-amplitude also has a high-frequency, while electrical stimulation having a high-amplitude also has a low-frequency. For example, electrical stimulation having an amplitude of a motor threshold value may also have a frequency of 10 Hertz. Further, electrical stimulation having an amplitude of one-half motor threshold value may also have a frequency of 5,000 Hertz.

In further examples, in which the stochastic function defines a series of values according to the unimodal or multimodal Gaussian probabilistic distribution, IMD 102 selects only those values within one standard deviation of the variance of the values in the Gaussian probabilistic distribution and uses the selected values within one standard deviation as values for the one or more parameters defining the electrical stimulation. For example, the one or more parameters of an example system include a pulse current amplitude and the stochastic function defines a unimodal half-normal probabilistic distribution having a mean centered on the maximum tolerable value. In this example, the maximum tolerable value is 7.8 milliamps and the stochastic function has a standard deviation of 1.56 milliamps. In the above example, IMD 102 selects only those values within 1.56 milliamps of 7.8 milliamps, e.g., a range of 6.24-7.8 milliamps as values for the one or more parameters defining the electrical stimulation. In other examples, IMD 102 selects only those values within two standard deviations of the variance of the Gaussian probabilistic distribution and uses the selected values within two standard deviations as values for the one or more parameters defining the electrical stimulation. Using the foregoing example, IMD 102 selects only those values within 2*1.56 milliamps of 7.8 milliamps, e.g., a range of 4.68-7.8 milliamps as values for the one or more parameters defining the electrical stimulation.

Using the series of values defined by the stochastic function, 1 MB 102 defines values for one or more parameters defining the electrical stimulation that vary over time. For example, the one or more parameters that vary over time based on the stochastic function may include one of a pulse current amplitude or a pulse voltage amplitude. As another example, IMD 102 defines values for the one or more parameters based on the stochastic function so as to add variation, noise, or jitter to an otherwise constant waveform of the electrical stimulation. Such variation of one or more parameters of the electrical stimulation, such as amplitude, may stimulation different fascicles and fibers of a larger nerve over time and with different stimulations, resulting in increased efficacy over systems that deliver continuous amplitude electrical stimulation. Further, the response of nerve fibers to the electrical stimulation may vary depending on the distance and orientation of the nerve fibers to the electrical stimulation. In other words, the nerve fiber response may be location-dependent (e.g., depend on whether the nerve fibers receive near-field or far-field electrical stimulation). Such variation of the one or more parameter values of the electrical stimulation over time may deliver near-field or far-field electrical stimulation to the nerve fibers, evoking varying responses from the nerve fibers over time. In some examples, the one or more parameters defining the electrical stimulation vary only based on the stochastic function. In other examples, IMD 102 varies the one or more parameters by both the stochastic function as well as in response to one or more sensed physiological signals of the patient or sensed ambient environmental conditions.

In the above examples, IMD 102 defines values for the one or more parameters defining the electrical stimulation that vary over time based on a stochastic function. However, these examples are provided for ease of discussion. In addition, or in the alternative to defining the one or more electrical stimulation therapy parameters based on the stochastic function, IMD 102 defines other types of complex variations to the at least one electrical stimulation parameter of the plurality of electrical stimulation parameters. For example, IMD 102 may introduce complex variation to the one or more electrical stimulation therapy parameters by introducing a ramping (e.g., sawtooth), periodic, oscillatory (e.g. sinusoidal), pulsatile, inverting, temporally applied, or transient function to the one or more electrical stimulation therapy parameters. In some examples, IMD 102 modifies the one or more electrical stimulation therapy parameters by introducing complex variation according to both a stochastic function and a ramping (e.g., sawtooth) function. In other examples, IMD 102 vary over time the one or more electrical stimulation therapy parameters according to a periodic function and not a stochastic function. In other examples, IMD 102 vary over time the one or more electrical stimulation therapy parameters according to a stochastic function only.

In some examples, the complex variation defines an amount (e.g., a percentage) of variation of the one or more electrical stimulation therapy parameters from a baseline value. In other examples, the complex variation defines a period of the variation of the one or more electrical stimulation therapy parameters, or a granularity of the variation of the one or more electrical stimulation therapy parameters (e.g., 10 different values, 500 different values, or 1,000 different values within a range from a baseline value of the one or more electrical stimulation therapy parameters). In other examples, the complex variation defines a metric for a complexity or randomness of the one or more electrical stimulation therapy parameters, such as a Kolmogorov complexity, or a number of different frequencies created as measurable through an Fourier analysis. Such examples are provided for ease of discussion and are not necessarily limiting. Other types of functions not expressly described herein may be used to add further variation to the waveform of the electrical stimulation.

IMD 102 controls delivery of the electrical stimulation to a target tissue site 118 of patient 112 and varies over time the one or more parameters of the electrical stimulation based on the stochastic function in the manner described above. As one example, for purposes of illustration, IMD 102 delivers continuous electrical stimulation having a fixed pulse width (e.g., of approximately 210 microseconds) and one of a fixed voltage or fixed current amplitude having a maximum tolerable value for the amplitude, as described above. Further, IMD 102 applies a stochastic function to the frequency of the electrical stimulation. In this example, the stochastic function defines a series of pseudo-random values for the frequency according to a unimodal Gaussian distribution having a median frequency of 10 Hertz, a coefficient of variation of ±0.2 to 0.8, and a range of 0.15 to 40 Hertz. In this case, frequency values of the stimulation may vary between 0.15 and 40 Hertz based on the stochastic function. Hence, in this example, the pulse amplitude and pulse width are fixed but the pulse rate, i.e., frequency, varies based on the stochastic function. In other examples, the frequency of the electrical stimulation is varied over time by varying a length of an inter-pulse interval based on the stochastic function, wherein, during the inter-pulse interval, no electrical stimulation is delivered.

In another example where IMD 102 delivers electrical stimulation therapy according to one or more parameters based on a stochastic function, IMD 102 delivers continuous electrical stimulation having a fixed frequency (e.g., of approximately 10 Hertz), a fixed pulse width (e.g., of approximately 210 microseconds), and an upper bound for a pulse current amplitude that is the maximum tolerable current amplitude, as described above. Further, IMD 102 applies a stochastic function to the pulse current amplitude of the electrical stimulation. In this example, the stochastic function defines a series of pseudo-random values for the pulse current amplitude according to a unimodal Gaussian distribution having a one-sided coefficient of variation of 0.2 to 0.8 and a range of 0 to 7.8 milliamps. Hence, in this example, the frequency and pulse width are fixed but the pulse current amplitude varies based on the stochastic function.

IMD 102 delivers such electrical stimulation to a target tissue 118 of patient 112, such as the brain, the spinal cord, pelvic nerves, peripheral nerves, or the gastrointestinal tract of a patient so as to deliver DBS, SCS, pelvic stimulation, gastric stimulation, or PNFS. IMD 102 delivers such electrical stimulation to suppress or reduce one or more symptoms of patient 112. For example, the one or more symptoms may include pelvic symptoms or pelvic dysfunctions of patient 112, such as over-active bladder (OAB) disease, urinary or fecal incontinence, pelvic pain, sexual dysfunction, gastroparesis, and other visceral or pelvic disorders. The one or more symptoms may further include chronic pain, tremor, Parkinson's disease, epilepsy, obesity, cognitive disorders, and movement disorders.

Systems designed to deliver electrical stimulation to a patient according to a constant amplitude and/or frequency over time can be implemented with relatively simple circuitry and control logic. However, electrical stimulation based on a stochastic function as described herein may present random or pseudo-random properties that may have greater efficacy in impacting both normal and dysfunctional tissues of the patient than electrical stimulation delivered according to simple signal waveforms alone. For example, as one illustration, electrical stimulation based on the stochastic function as described herein to a sacral nerve of the patient may exhibit increased bladder quieting responses over electrical stimulation having a constant amplitude.

Figure 2:
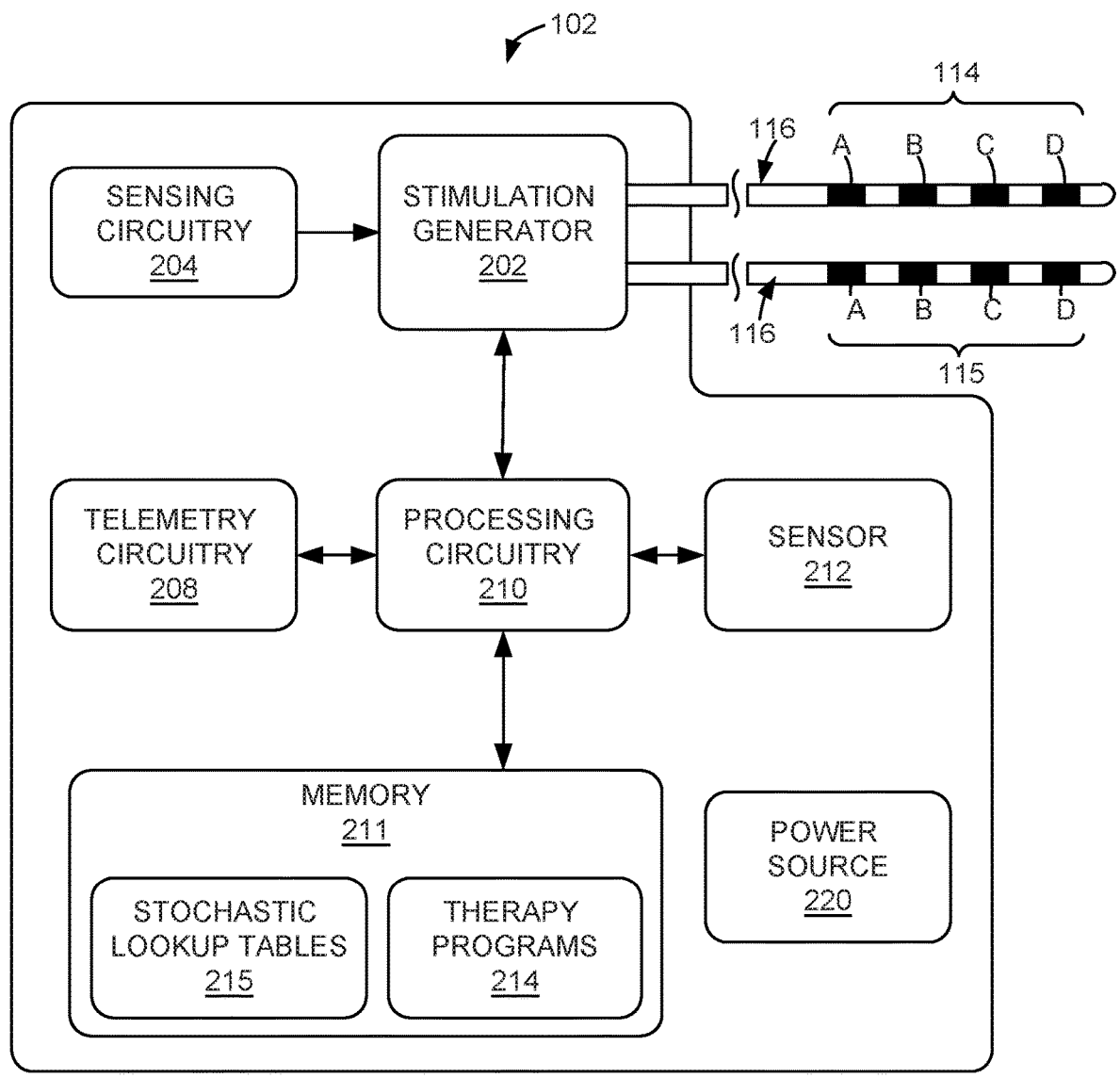
FIG. 2 is a block diagram of the example IMD of FIG. 1.

FIG. 2 is a block diagram of the example IMD 102 of FIG. 1. In the example shown in FIG. 2, IMD 102 includes processing circuitry 210, memory 211, stimulation generator 202, sensing circuitry 204, telemetry circuitry 208, sensor 212, and power source 220. Each of these circuitry blocks may be or include electrical circuitry configured to perform the functions attributed to each respective circuitry block. For example, processing circuitry 210 may include one or more processors, stimulation generator 202 may include switch circuitry, sensing circuitry 204 may include sensing circuitry, and telemetry circuitry 208 may include telemetry circuitry. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines one or more parameters of the electrical stimulation therapy, such as a stimulation electrode combination (i.e., active electrodes used to deliver the stimulation), electrode polarities, current or voltage amplitude, pulse width, pulse rate, and duty cycle. In some examples, the electrical stimulation parameters define a waveform for the electrical stimulation, such as rectangular or non-rectangular, rising exponentials, falling exponentials, or sinusoidal. Different waveforms may modulate the axon population differently, and may be selected so as to adjust the tissue area of patient 112 that receives electrical stimulation. In some examples, individual therapy programs may be stored as a therapy group, which defines a set of therapy programs with which stimulation may be generated.

Stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generator 202 according to therapy programs 214 stored in memory 211 to apply particular stimulation parameter values specified by one or more of programs, such as amplitude, pulse width, pulse rate, and duty cycle.

In the example shown in FIG. 2, the set of electrodes 114 includes electrodes 114A, 114B, 114C, and 114D, and the set of electrodes 115 includes electrodes 115A, 115B, 115C, and 115D. Processing circuitry 210 also controls stimulation generator 202 to generate and apply the stimulation signals to selected combinations of electrodes 114, 115. In some examples, stimulation generator 202 includes switch circuitry that couples stimulation signals to selected conductors within leads 16, which, in turn, deliver the stimulation signals across selected electrodes 114, 115. Such switch circuitry may be a switch array, switch matrix, multiplexer, or any other type of switching circuitry configured to selectively couple stimulation energy to selected electrodes 114, 115 and to selectively sense bioelectrical neural signals of spine 20 with selected electrodes 114, 115.

In other examples, however, stimulation generator 202 comprises a plurality of pairs of voltage sources, current sources, voltage sinks, or current sinks connected to each of electrodes 114, 115 such that each pair of electrodes has a unique signal generator. In other words, in these examples, each of electrodes 114, 115 is independently controlled via its own signal generator (e.g., via a combination of a regulated voltage source and sink or regulated current source and sink), as opposed to switching signals between electrodes 114, 115.

Stimulation generator 202 may be a single channel or multi-channel stimulation generator. In particular, stimulation generator 202 may be capable of delivering a single stimulation pulse or multiple stimulation pulses at a given time via a single electrode combination or multiple stimulation pulses at a given time via multiple electrode combinations. In some examples, however, stimulation generator 202 may be configured to deliver multiple channels on a time-interleaved basis. For example, switch circuitry of stimulation generator 202 may serve to time divide the output of stimulation generator 202 across different electrode combinations at different times to deliver multiple programs or channels of stimulation energy to patient 112.

In another example, the stimulation generator 202 may control the independent sources or sinks on a time-interleaved bases. In some examples, stimulation generator 202 cycles through different stimulation parameters in blocks. In other examples, stimulation generator 202 interleaves different stimulation parameters with one another to create a composite electrical stimulation program. In yet further examples, stimulation generator 202 cycles between periods of time where electrical stimulation is delivered and periods of time in which no electrical stimulation is delivered. In such examples, processor 210 may control stimulation generator 202 to vary the length of a duty cycle of the period (e.g., the ratio of time where electrical stimulation is delivered versus the total length of the period) based on the stochastic function. In some examples, stimulation generator 202 includes circuitry configured to provide active or passive charge balancing so as to balancing electrical charge induced by delivery of the electrical stimulation.

Electrodes 114, 115 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. In one example, the electrodes may be electrically coupled to stimulation generator 202 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing circuitry 204 is incorporated into a common housing with stimulation generator 202 and processing circuitry 210 in FIG. 2, in other examples, sensing circuitry 204 may be in a separate housing from IMD 102 and may communicate with processing circuitry 210 via wired or wireless communication techniques. Example bioelectrical signals include, but are not limited to, a signal generated from local field potentials within one or more regions of spine 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to the patient).

Telemetry circuitry 208 supports wireless communication between IMD 102 and an external programmer 104 or another computing device under the control of processing circuitry 210. Processing circuitry 210 of IMD 102 may receive, as updates to programs, values for various stimulation parameters such as amplitude and electrode combination, from programmer 104 via telemetry circuitry 208. The updates to the therapy programs may be stored within therapy programs 214 portion of memory 211. Telemetry circuitry 208 in IMD 102, as well as telemetry circuitry in other devices and systems described herein, such as programmer 104, may accomplish communication by radiofrequency (RF) communication techniques. In addition, telemetry circuitry 208 may communicate with external medical device programmer 104 via proximal inductive interaction of IMD 102 with programmer 104. Accordingly, telemetry circuitry 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

Telemetry circuitry 208 of IMD 102 receives commands from an external programmer 104. In response to these commands, processing circuitry 210 of IMD 102 controls stimulation generator 202 to deliver electrical stimulation therapy programs to a target tissue area of the spinal column 20 of patient 112 via electrodes 114, 115 of leads 16.

According to the techniques of this disclosure, processing circuitry 210 modifies one or more electrical stimulation parameters by introducing complex variation to the one or more electrical stimulation parameters, and controls stimulation generator 202 to deliver electrical stimulation therapy according to the modified one or more electrical stimulation parameters to a target tissue site of patient 112 to provide therapy for one or more pelvic symptoms of patient 112. In some examples, processing circuitry 210 applies a stochastic function to generate a series of values having a probabilistic distribution. Processing circuitry 210 stores the series of values having the probabilistic distribution in one or more stochastic lookup tables 215 within memory 211. Processing circuitry 210 selects values from the series of values stored in lookup tables 215 and uses the selected values to define values of the one or more parameters defining the electrical stimulation therapy. Processing circuitry 210 of IMD 102 controls stimulation generator 202 to deliver, to patient 12 and via a plurality of electrode combinations of electrodes 114, 115 of leads 16, electrical stimulation therapy according to the one or more parameters. In this fashion, processing circuitry 210 may define one or more parameters of the electrical stimulation based on the stochastic function so as to impart a degree of randomness to the electrical stimulation delivered to the patient. For example, variation of one or more parameters of the electrical stimulation, such as varying amplitude values, may stimulate different fascicles and fibers of a larger nerve over time. The result may increase efficacy over systems that deliver electrical stimulation with a single amplitude value. Further, the response of nerve fibers to the electrical stimulation may vary depending on the distance and orientation of the nerve fibers to the electrical stimulation. In other words, the nerve fiber response may be location-dependent (e.g., depend on whether the nerve fibers receive near-field or far-field electrical stimulation). Such variation of the one or more parameter values of the electrical stimulation over time may deliver near-field or far-field electrical stimulation to the nerve fibers, evoking varying responses from the nerve fibers over time.

In some examples, processing circuitry 210 selects subsequent values from the series of values of stochastic lookup tables 215 and uses each subsequent value to define a subsequent value of the one or more parameters defining the electrical stimulation therapy. In one example, processing circuitry 210 uses an index counter as an index into stochastic lookup tables 215 to select values from stochastic lookup tables 215 to define values of the one or more parameters defining the electrical stimulation therapy. In some examples, processing circuitry 210 increments this index counter after a predetermined time. In further examples, processing circuitry increments this index counter according to a pulse rate and pulse width of the electrical stimulation. For example, in a system where the pulse width is 210 microseconds and the inter-pulse interval is 99,790 microseconds, processing circuitry 210 increments the index counter after 100,000 microseconds. In other examples, processing circuitry 210 increments the index counter after controlling stimulation generator 202 to deliver a predetermined number of electrical stimulation pulses to patient 112. This predetermined number may be a single electrical stimulation pulse, a plurality of electrical stimulation pulses (e.g., a pulse train of two or more pulses), or a group of electrical stimulation pulses delivered together followed by a period of time wherein electrical stimulation is not delivered (e.g., a pulse burst). In some examples, the predetermined number is a function of pulse rate and pulse width of the electrical stimulation. Thus, as processing circuitry 210 increments the index counter over time, processing circuitry 210 advances through the values stored in stochastic lookup tables 215.

In some examples, after advancing the index counter throughout stochastic lookup tables 215 and controlling stimulation generator 202 to deliver electrical stimulation having the one or more parameters defined by each value of stochastic lookup tables 215, processing circuitry 210 applies the stochastic function to generate a new series of values having a probabilistic distribution and stores the new series of values in stochastic lookup tables 215. The new series of values may be different from the previous series of values. Further, the new series of values may vary according to a different stochastic function than the previous series of values. For example, upon using each of a previous series of values to define a value of the one or more parameters defining the electrical stimulation therapy, processing circuitry 210 generates a new series of values based on the stochastic function. Processing circuitry overwrites the previous series of values in stochastic lookup tables 215 with this new series of values. Further, processing circuitry resets the index counter to zero. In alternate examples, processing circuitry 210 regenerates the series of values stored in stochastic lookup tables 215 after using a subset of the series of values to define the one or more parameters defining the electrical stimulation therapy, such as ten, twenty, or fifty values stored in stochastic lookup tables 215.

In further examples, processing circuitry 210 generates the series of values stored in stochastic lookup tables 215 once, and reuses the series of values stored in stochastic lookup tables 215 to generate pseudo-random values for the one or more parameters defining the electrical stimulation therapy. In yet further examples, a separate computer uploads or stores the series of values stored in stochastic lookup tables 215 at the time of manufacturing or assembly of IMD 102.

In yet further examples, rather than using lookup tables 215, processing circuitry 210 functions as a random number generator and generates, based on the stochastic function, a plurality of random values within pre-specified bounds. Processing circuitry 210 uses each random value as a value for the one or more parameters of the electrical stimulation therapy that vary over time according to the stochastic function. In this example, processing circuitry 210 generates a new random number for each electrical stimulation pulse in real time as electrical stimulation therapy is delivered to patient 112.

In further examples, processing circuitry 210 stores a series of ordered values in stochastic lookup tables 215. In this example, each time that processing circuitry 210 retrieves a value from stochastic lookup tables 215, processing circuitry 210 applies the stochastic function to the index to determine a pseudo-random index that results in retrieving a pseudo-random value from stochastic lookup tables 215.

Processing circuitry 210 controls stimulation generator 202 to deliver the electrical stimulation to a target tissue site 118 of patient 112. Processing circuitry 210 further controls stimulation generator 202 to vary over time the one or more parameters of the electrical stimulation based on the stochastic function in the manner described above. As one example, processing circuitry 210 controls stimulation generator 202 to deliver continuous electrical stimulation having a fixed pulse width of 210 microseconds and one of a fixed voltage or current amplitude having a maximum tolerable value for the amplitude, as described above. Further, processing circuitry 210 applies a stochastic function to the frequency of the electrical stimulation delivered by stimulation generator 202. In this example, the stochastic function defines a series of pseudo-random values for the frequency according to a unimodal Gaussian distribution having a median frequency of 10 Hertz, a coefficient of variation of ±0.2 to 0.8, and a range of 0.15 to 40 Hertz.

In another example where IMD 102 delivers electrical stimulation therapy according to one or more parameters based on a stochastic function, processing circuitry 210 controls stimulation generator 202 to deliver continuous electrical stimulation having a fixed frequency of 10 Hertz, a fixed pulse width of 210 microseconds, and an upper bound for a pulse current amplitude that is the maximum tolerable current amplitude, as described above. Further, processing circuitry 210 applies a stochastic function to the pulse current amplitude of the electrical stimulation delivered by stimulation generator 202. In this example, the stochastic function defines a series of pseudo-random values for the pulse current amplitude according to a unimodal Gaussian distribution having a one-sided coefficient of variation of 0.2 to 0.8 and a range of 0 to 7.8 milliamps.

Processing circuitry 210 controls stimulation generator 202 to deliver such electrical stimulation to a target tissue 118 of patient 112, such as the brain, the spinal cord, pelvic nerves, peripheral nerves, or the gastrointestinal tract of a patient so as to deliver DBS, SCS, pelvic stimulation, gastric stimulation, or PNFS. Processing circuitry 210 controls stimulation generator 202 to deliver such electrical stimulation to suppress or reduce one or more symptoms of patient 112. For example, the one or more symptoms may include pelvic symptoms or pelvic dysfunctions of patient 112, such as over-active bladder (OAB) disease, urinary or fecal incontinence, pelvic pain, sexual dysfunction, gastroparesis, and other visceral or pelvic disorders. The one or more symptoms may further include chronic pain, tremor, Parkinson's disease, epilepsy, obesity, cognitive disorders, and movement disorders.

In the example of FIG. 2, IMD 102 uses stochastic look-up tables 215 to implement the stochastic function; however, stochastic look-up tables 215 are only one example of the implementation. In other examples, stimulation generator 202 does not require stochastic look-up tables 215 to deliver electrical stimulation and vary the one or more parameters of the electrical stimulation according to the stochastic function. For example, stimulation generator 202 of IMD 102 may include software or dedicated hardware circuitry configured to deliver electrical stimulation according to a pre-defined stochastic function. In such an example, the pre-defined function may be configured by the clinician or preconfigured during manufacturing, and stimulation generator 202 may deliver electrical stimulation having one or more parameters that vary over time without a need to reference stochastic look-up tables 215.

Figure 3:
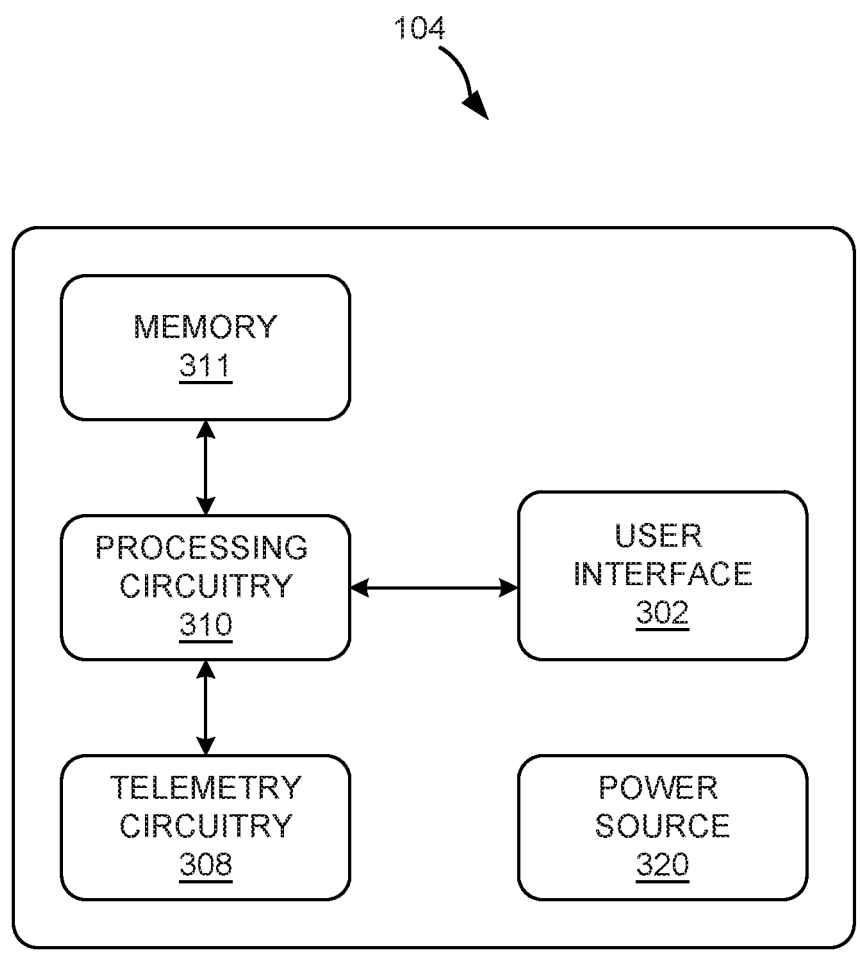
FIG. 3 is a block diagram of the example external programmer of FIG. 1.

FIG. 3 is a block diagram of an example external programmer 104 of FIG. 1, such as programmer 104A or programmer 104B. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or circuitry, may include electrical circuitry that is configured to perform some or all of the functionality described herein. For example, processing circuitry 310 may include one or more processors configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate circuits, in some examples, processing circuitry 310 and telemetry circuitry 308 are functionally integrated. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain one or more parameters from memory, or receive a user input and send a corresponding command to IMD 104, or instructions for any other functionality. In addition, memory 311 may include a plurality of therapy programs 214, where each program includes one or more parameters that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, or the input may request some other change to the delivery of electrical stimulation.

Telemetry circuitry 308 may support wireless communication between IMD 102 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry circuitry 308 may be configured to transmit a spatial electrode movement pattern or other stimulation parameter values to IMD 102 for delivery of stimulation therapy.

In some examples, selection of therapy parameters or therapy programs may be transmitted to a medical device (e.g., IMD 102) for delivery to patient 112. In other examples, the therapy may include medication, activities, or other instructions that patient 112 must perform themselves or a caregiver perform for patient 112. In some examples, programmer 104 may provide visual, audible, and/or tactile notifications that indicate there are new instructions. Programmer 104 may require receiving user input acknowledging that the instructions have been completed in some examples.

According to the techniques of the disclosure, all or a portion of the periodic or stochastic function defining the complex variation may be located on external programmer 104. For example, processing circuitry 310, in response to commands received from a clinician or patient via a user interface 302, may transmit commands via telemetry circuitry 308 causing IMD 102 to deliver electrical stimulation therapy based on a stochastic function to a target tissue site of patient 112 to provide therapy for one or more pelvic symptoms of patient 112. In some examples, a clinician receives, via user interface 302, a list of stochastic functions. The clinician selects, via user interface 302, a specific stochastic function with which to deliver the electrical stimulation to patient 112. Processing circuitry 310 issues instructions, via telemetry circuitry 301, to IMD 102 causing IMD 102 to control delivery of the electrical stimulation to target tissue site 118 of patient 112 and vary over time the one or more parameters of the electrical stimulation based on the selected stochastic function. Alternatively, processing circuitry 310 generates values for the one or more parameters based on the stochastic function and uploads, via telemetry circuitry 301, the values for the one or more parameters to IMD 102, causing IMD 102 to control delivery of the electrical stimulation to target tissue site 118 of patient 112 and vary over time the one or more parameters of the electrical stimulation based on the selected stochastic function.

As one example, a clinician selects, via user interface 302, an electrical stimulation therapy program comprising continuous electrical stimulation having a fixed pulse width of 210 microseconds and one of a fixed voltage or current amplitude having a maximum tolerable value for the amplitude, as described above. Further, the clinician selects, via user interface 302, a stochastic function defining a series of pseudo-random values for the frequency of the electrical stimulation according to a unimodal Gaussian distribution having a median frequency of 10 Hertz, a coefficient of variation of ±0.2 to 0.8, and a range of 0.15 to 40 Hertz. In one example, processing circuitry 310 issues instructions, via telemetry circuitry 301, to IMD 102 causing IMD 102 to control delivery of the electrical stimulation to target tissue site 118 of patient 112 according to the selected electrical stimulation therapy program. Further, processing circuitry 310 issues instructions, via telemetry circuitry 301, to IMD 102 causing IMD 102 to vary over time the one or more parameters of the electrical stimulation based on the selected stochastic function. Alternatively, processing circuitry 310 generates values for the one or more parameters according to the selected stochastic function and uploads, via telemetry circuitry 301, the values for the one or more parameters to IMD 102, causing IMD 102 to control delivery of the electrical stimulation to target tissue site 118 of patient 112 and vary over time the one or more parameters of the electrical stimulation based on the selected stochastic function.

As a further example, a clinician selects, via user interface 302, an electrical stimulation therapy program comprising continuous electrical stimulation having a fixed frequency of 10 Hertz, a fixed pulse width of 210 microseconds, and an upper bound for a pulse current amplitude that is the maximum tolerable current amplitude, as described above. Further, the clinician may select, via user interface 302, a stochastic function defining a series of pseudo-random values for the pulse current amplitude of the electrical stimulation according to a unimodal Gaussian distribution having a one-sided coefficient of variation of 0.2 to 0.8 and a range of 0 to 7.8 milliamps. Processing circuitry 310 issues instructions, via telemetry circuitry 301, to IMD 102 causing IMD 102 to control delivery of the electrical stimulation to target tissue site 118 of patient 112 according to the selected electrical stimulation therapy program. As one example, processing circuitry 310 issues instructions, via telemetry circuitry 301, to IMD 102 causing IMD 102 to vary over time the one or more parameters of the electrical stimulation based on the selected stochastic function. Alternatively, processing circuitry 310 generates values for the one or more parameters according to the selected stochastic function and uploads, via telemetry circuitry 301, the values for the one or more parameters to IMD 102, causing IMD 102 to control delivery of the electrical stimulation to target tissue site 118 of patient 112 and vary over time the one or more parameters of the electrical stimulation based on the selected stochastic function.

Figure 4:
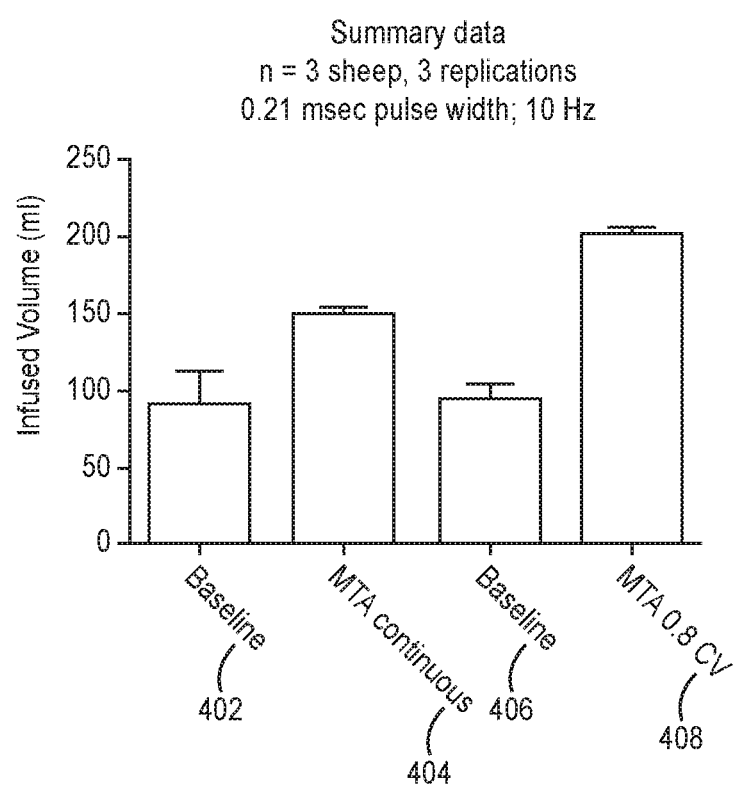
FIG. 4 is a graph illustrating example results of a system configured to deliver electrical stimulation therapy having a pulse current amplitude that is varied based on a stochastic function to a patient.

FIG. 4 is a graph illustrating example results of a system configured to deliver electrical stimulation therapy having a pulse current amplitude that is varied based on a stochastic function to a sheep. In the example of FIG. 4, the bladder capacity of three sheep were measured at normal baseline capacities 402 and 406, in the presence of conventional electrical stimulation therapy 404, and electrical stimulation therapy 408 comprising a pulse current amplitude that varies over time based on a stochastic function.

As depicted in the graph of FIG. 4, the sheep exhibited a bladder capacity of less than 100 milliliters at baselines 402, 406 (e.g., in the absence of electrical stimulation). A first electrical stimulation therapy 404 was applied to the sheep. The first electrical stimulation therapy was a conventional, continuous electrical stimulation having a fixed pulse width of 210 microseconds, a fixed current amplitude of 3.8 milliamps and a fixed frequency of 10 Hertz). While receiving such electrical stimulation 404, the sheep exhibited a bladder capacity of approximately 150 milliliters (e.g., a 67% increase over the baseline).

Further, the sheep received a second electrical stimulation 408 having one or more parameters that varies over time based on a stochastic function. In particular, the second electrical stimulation 408 comprised continuous electrical stimulation having a fixed pulse width of 210 microseconds and a fixed frequency of 10 Hertz. Further, the pulse current varies over time based on a stochastic function defining a half-normal probabilistic distribution having a coefficient of variance of 0.8 and a maximum tolerable value for the amplitude acting as a maximum cutoff for values of the pulse current. While receiving such electrical stimulation 406 that varies over time based on the stochastic function, the sheep exhibited a bladder capacity of approximately 200 milliliters (e.g., an 116% increase over the baseline). Thus, electrical stimulation with pulse current amplitude that varies over time based on a stochastic function, as described herein, may have greater efficacy in impacting both normal and dysfunctional tissues of the patient than electrical stimulation delivered according to simple signal waveforms alone. For example, delivery of electrical stimulation with a pulse current amplitude varied based on the stochastic function as described herein to a sacral nerve of the patient may exhibit increased bladder quieting responses over electrical stimulation having a constant amplitude, producing greater effective bladder capacity. Thus, such electrical stimulation may exhibit greater efficacy than conventional electrical stimulation therapies.

Figure 5:
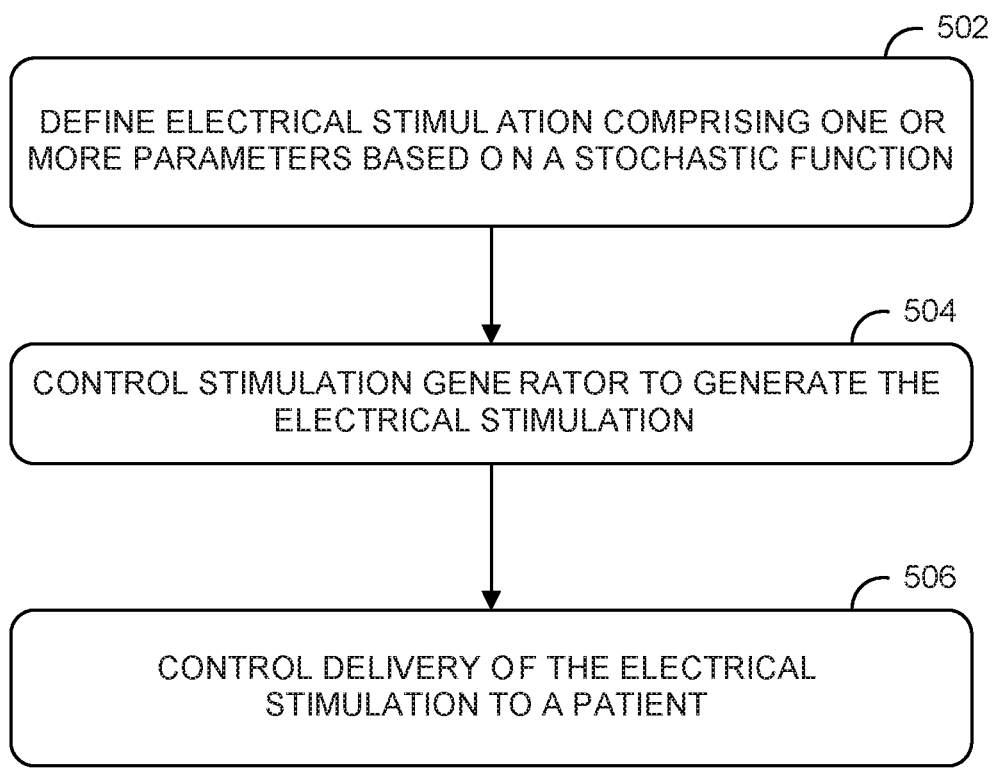
FIG. 5 is a flowchart depicting an example operation for the IMD of FIG. 1.

FIG. 5 is an illustration depicting an example operation for the IMD 102 of FIG. 1. For ease of description, FIG. 5 is described with respect to FIGS. 1 and 2. With respect to the example of FIG. 5, a clinician, via external programmer 104, configures one or more electrical stimulation therapy parameters to define at least one pulse train of electrical stimulation that IMD 102 delivers to patient 112 to provide neuromodulation therapy to patient 112. For instance, the clinician may configure the one or more electrical stimulation therapy parameters to a baseline level during a clinical or outpatient visit. In some examples, the clinician configures the one or more electrical stimulation therapy parameters based on patient feedback.

As depicted in FIG. 5, processing circuitry 210 of IMD 102 identifies the one or more electrical stimulation parameters for the at least one pulse train of the electrical stimulation. For example, processing circuitry 210 may select one or more of a pulse voltage amplitude or a pulse current amplitude of the electrical stimulation, a recharge interval of the electrical stimulation, a pulse width of the electrical stimulation, a duty cycle of the electrical stimulation, a pulse frequency, and/or an inter-stimulation interval of the electrical stimulation to be modified according to a complex variation. In some examples, the clinician may predetermine which of the one or more parameters may be modified and enable, via external programmer 104, IMD 102 to select particular electrical stimulation parameters to be modified.

Processing circuitry 210 of IMD 102 defines a complex variation to the identified one or more electrical stimulation parameters to reduce a pelvic symptom of the patient. In some examples, the complex variation is based on a periodic function or a stochastic function. In the example of FIG. 5, processing circuitry 210 of IMD 102 defines the one or more parameters of electrical stimulation based on a stochastic function (502). In some examples, the one or more symptoms may include pelvic symptoms or pelvic dysfunctions of patient 112, such as over-active bladder (OAB) disease, urinary or fecal incontinence, pelvic pain, sexual dysfunction, gastroparesis, and other visceral or pelvic disorders.

Processing circuitry 210 of IMD 102 modifies the at least one pulse train of electrical stimulation by introducing the complex variation to the one or more electrical stimulation parameters. With respect to the example of FIG. 5, IMD 102 uses the stochastic function to determine a series of values for one or more of a pulse voltage amplitude or a pulse current amplitude of the electrical stimulation, a recharge interval of the electrical stimulation, a pulse width of the electrical stimulation, a duty cycle of the electrical stimulation, a pulse frequency, and/or an inter-stimulation interval of the electrical stimulation.

In some examples, the stochastic function defines a probabilistic distribution of values. Values of the probabilistic distribution may be used as values of the one or more parameters defining the electrical stimulation. For example, the stochastic function may define a uniform probabilistic distribution of values. In other examples, the stochastic function defines a non-uniform probabilistic distribution of values, such as a unimodal or multimodal Gaussian probabilistic distribution, a log-normal probabilistic distribution, a binomial probabilistic distribution, a geometric probabilistic distribution, or an exponential probabilistic distribution. In yet further examples, the stochastic function may apply an equation to define the probabilistic distribution of values.

In the above examples, processing circuitry 210 defines one or more parameters of the electrical stimulation that vary over time based on a stochastic function. However, in addition, or in the alternative to defining the one or more electrical stimulation therapy parameters based on the stochastic function, processing circuitry 210 further defines the one or more parameters of the electrical stimulation based on other types of functions. For example, processing circuitry 210 may further vary over time the one or more parameters of the electrical stimulation according to a ramping, periodic, oscillatory, pulsatile, inverting, temporally applied, or transient function. Such other types of functions may add further variation to the waveform of the electrical stimulation.

Further, processing circuitry 210 controls stimulation generator 202 to generate the at least one pulse train based on the modified one or more electrical stimulation therapy parameters. In the example of FIG. 5, processing circuitry 210 controls stimulation generator 202 to generate the electrical stimulation comprising the one or more parameters based on the stochastic function (504). As one example, processing circuitry 210 controls stimulation generator 202 to generate an electrical stimulation waveform that has one of a pulse current amplitude or a pulse voltage amplitude that varies over time based on the stochastic function. As another example, processing circuitry 210 controls stimulation generator 202 to add variation, noise, or jitter to an otherwise constant waveform of the electrical stimulation. In some examples, processing circuitry 210 controls stimulation generator 202 to vary over time the one or more parameters defining the electrical stimulation only based on the stochastic function. In other examples, processing circuitry 210 controls stimulation generator 202 to vary over time the one or more parameters by both the stochastic function as well as in response to one or more sensed physiological signals of the patient or sensed ambient environmental conditions. Such variation of one or more parameters of the electrical stimulation, such as amplitude, may stimulation different fascicles and fibers of a larger nerve over time and with different stimulations, resulting in increased efficacy over systems that deliver continuous amplitude electrical stimulation. Further, the efficacy of electrical stimulation to nerve fibers may be location-dependent, and induce varying responses depending on whether the nerve fibers receive near-field or far-field electrical stimulation.

Processing circuitry 210 controls stimulation generator 202 to deliver the electrical stimulation comprising the modified one or more electrical stimulation therapy parameters to a target tissue site 118 of patient 112. With respect to FIG. 5, processing circuitry 210 controls stimulation generator 202 to deliver the electrical stimulation comprising the one or more parameters based on the stochastic function to a target tissue site 118 of patient 112 (506). Examples of target tissue site 118 include the brain, the spinal cord, pelvic nerves, peripheral nerves, or the gastrointestinal tract of patient 112 so as to deliver DBS, SCS, pelvic stimulation, gastric stimulation, or PNFS. Processing circuitry 210 controls stimulation generator 202 to deliver such electrical stimulation to suppress or reduce one or more symptoms of patient 112. For example, the one or more symptoms may include pelvic symptoms or pelvic dysfunctions of patient 112, such as over-active bladder (OAB) disease, urinary or fecal incontinence, pelvic pain, sexual dysfunction, gastroparesis, and other visceral or pelvic disorders. The one or more symptoms may further include chronic pain, tremor, Parkinson's disease, epilepsy, obesity, cognitive disorders, and movement disorders.

Figure 6:
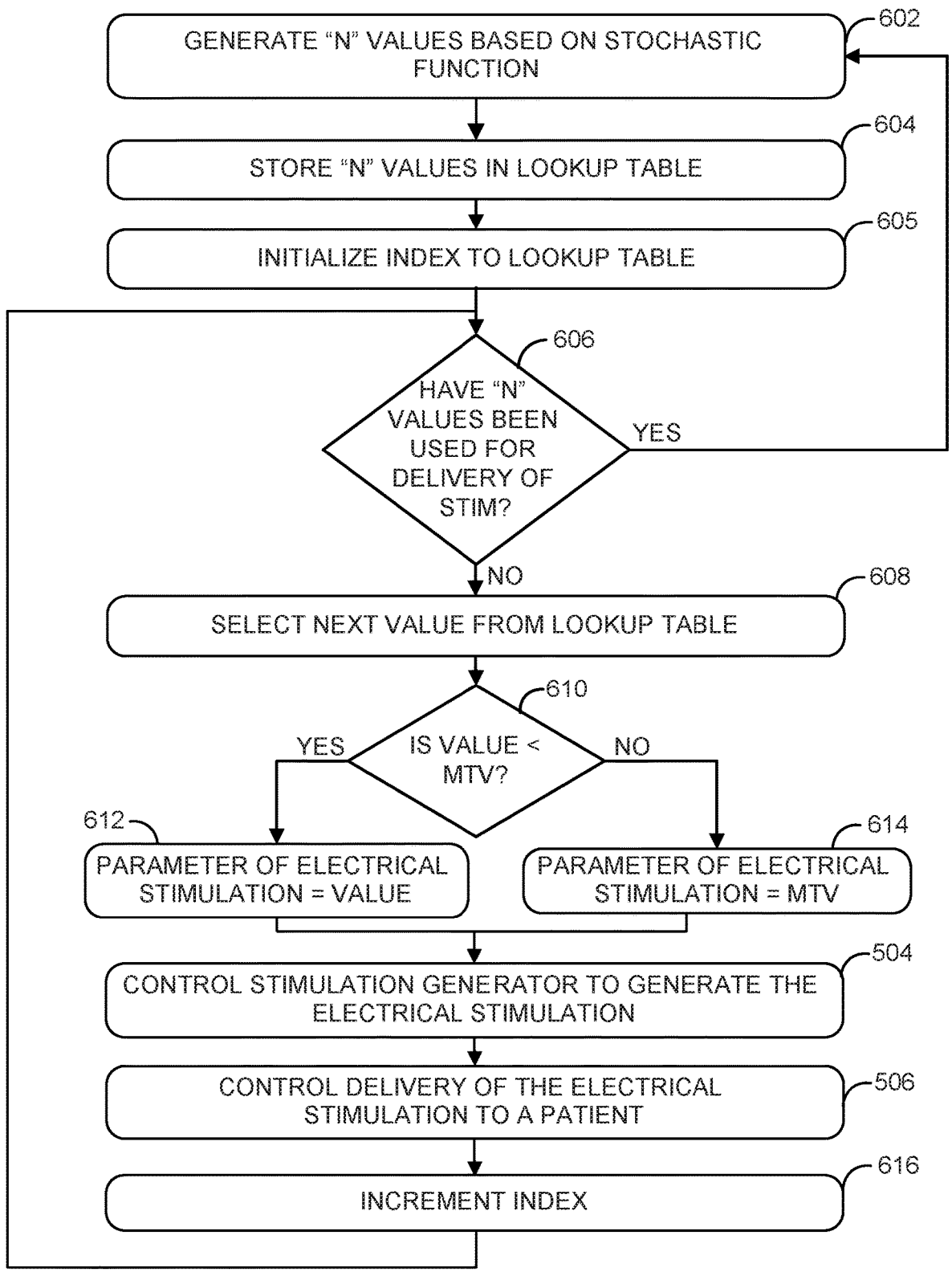
FIG. 6 is a flowchart depicting an example operation for the IMD of FIG. 1.

FIG. 6 is a flowchart depicting an example operation for the IMD of FIG. 1. For ease of description, FIG. 5 is described with respect to FIGS. 1 and 2. As depicted in FIG. 5, processing circuitry 210 of IMD 102 generates a series of values based on a stochastic function (602). The series may be repeated upon use of the last value in the series. In this example, the series is of "N" length, where "N" represents any integer. It has been discovered that the series length "N" can have a meaningful effect on the effectiveness of the stimulation. Without being limited by theory, experimental testing suggests that a sufficiently large value for "N" can be relevant to achieving improvements provided through the introduction of complex stimulation parameters. For example, "N" may be an integer large enough to ensure that, when delivering electrical stimulation comprising one or more parameters defined by the series of "N" values based on a stochastic function, the electrical stimulation exhibits meaningful therapeutic improvement. According to various embodiments, a particular value for "N" can be determined relative to the device parameters, stimulation type, and desired therapy. In some examples, "N" is about 500, about 990, or about 1000. In certain examples, "N" may be selected based on a capacity of memory 211 that implements stochastic lookup tables 215.

In some examples, the stochastic function defines a probabilistic distribution of values. For example, the stochastic function may define a uniform probabilistic distribution of values. In other examples, the stochastic function defines a non-uniform probabilistic distribution of values, such as a unimodal or multimodal Gaussian probabilistic distribution, a log-normal probabilistic distribution, a binomial probabilistic distribution, a geometric probabilistic distribution, or an exponential probabilistic distribution. In yet further examples, the stochastic function may apply an equation to define the probabilistic distribution of values.

In the above examples, processing circuitry 210 defines one or more parameters of the electrical stimulation that vary over time based on the stochastic function. However, in addition, or in the alternative to defining the one or more electrical stimulation therapy parameters based on the stochastic function, processing circuitry 210 further modifies the one or more parameters of the electrical stimulation by introducing complex variation based on other types of functions. For example, processing circuitry 210 may further modify the one or more parameters of the electrical stimulation by applying a ramping, periodic, oscillatory, pulsatile, inverting, temporally applied, or transient function to the one or more parameters of the electrical stimulation. Such other types of functions may add further variation to the waveform of the electrical stimulation.

Upon generating the series of values, processing circuitry 210 stores the series of values in stochastic lookup tables 215 (604). In some examples, processing circuitry 210 initializes or clears an index counter for indexing into stochastic lookup tables 215 (605). Processing circuitry 210 determines whether a number "N" of the series of values stored in stochastic lookup tables 215 have been used (606). If the number "N" of the series of values stored in stochastic lookup tables 215 have not been used (e.g., "NO" block of 606), processing circuitry 210 uses the index counter to select a next value from stochastic lookup tables 215 (608).

In some examples, a clinician determines a maximum tolerable value, as described above. In these examples, the maximum tolerable value acts as a maximum upper bound for series of values based on the stochastic function. In other words, the stochastic function defines, according to the probabilistic distribution, the series of values that are used to define the one or more parameters that define the electrical stimulation delivered to patient 112. Further, each of the series of values are less than or equal to the maximum tolerable value for the one or more parameters defining the electrical stimulation, so as to prevent delivering electrical stimulation above the maximum tolerable value.

For example, upon selecting the next value from stochastic lookup tables 215, processing circuitry 210 determines whether the selected value is less than or equal to the maximum tolerable value (610). Upon determining that the selected value is less than or equal to the maximum tolerable value (e.g., "YES" block of 610), processing circuitry 210 sets one or more parameters of the electrical stimulation to the selected value (612). Upon determining that the selected value is greater than the maximum tolerable value (e.g., "NO" block of 610), processing circuitry 210 sets one or more parameters of the electrical stimulation to the maximum tolerable value (614).

Processing circuitry 210 controls stimulation generator 202 to generate the electrical stimulation comprising the one or more parameters based on the stochastic function in a similar fashion as described with respect to FIG. 5. (504). Further, Processing circuitry 210 controls stimulation generator 202 to deliver the electrical stimulation comprising the one or more parameters based on the stochastic function to a target tissue site 118 of patient 112 in a similar fashion as described with respect to FIG. 5 (506).

Upon delivering the electrical stimulation, processing circuitry 210 increments the index counter (616). In some examples, processing circuitry 210 increments the index counter after controlling stimulation generator 202 to deliver a predetermined number of electrical pulses. In one example, processing circuitry 210 increments the index counter after controlling stimulation generator 202 to deliver a single pulse or a train of a plurality of pulses, wherein the length of the pulse train is specified by the clinician. In other examples, processing circuitry 210 increments the index counter after controlling stimulation generator 202 to deliver electrical stimulation for a predetermined time. In one example, processing circuitry 210 increments the index counter after controlling stimulation generator 202 to deliver electrical stimulation for a duration approximately equal to a length of one pulse of the electrical stimulation. In other examples, processing circuitry 210 increments the index counter after controlling stimulation generator 202 to deliver electrical stimulation for a period of time specified by the clinician.

After incrementing the counter, processing circuitry 210 determines whether a number "N" of the series of values stored in stochastic lookup tables 215 have been used (606). If the number "N" of the series of values stored in stochastic lookup tables 215 have not been used (e.g., "NO" block of 606), processing circuitry 210 uses the index counter to select a next value from stochastic lookup tables 215 (608).

If the number "N" of the series of values stored in stochastic lookup tables 215 have been used (e.g., "YES" block of 606), then processing circuitry 210 generates a new series of values based on the stochastic function (602). The new series of values may be different from the previous series of values. Further, the new series of values may vary according to a different stochastic function than the previous series of values. Processing circuitry overwrites the previous series of values in stochastic lookup tables 215 with this new series of values (604) and resets the index counter to zero (605).

Thus, by incrementing the index counter over time, processing circuitry 210 retrieves successive values from stochastic lookup tables 215 that vary over time, causing processing circuitry 210 to control stimulation generator 202 to generate and deliver electrical stimulation having one or more parameters that vary over time. Further, upon using all or a portion of the series of values stored within stochastic lookup tables 215, processing circuitry 210 may regenerate a new series of values according to the same or a different stochastic function, further imparting a degree of randomness to one or more parameters of the electrical stimulation so as to stimulate a greater cross section of nerve fibers and tissue of the patient than is possible with electrical stimulation that does not vary over time based on the stochastic function.

Figure 7A:
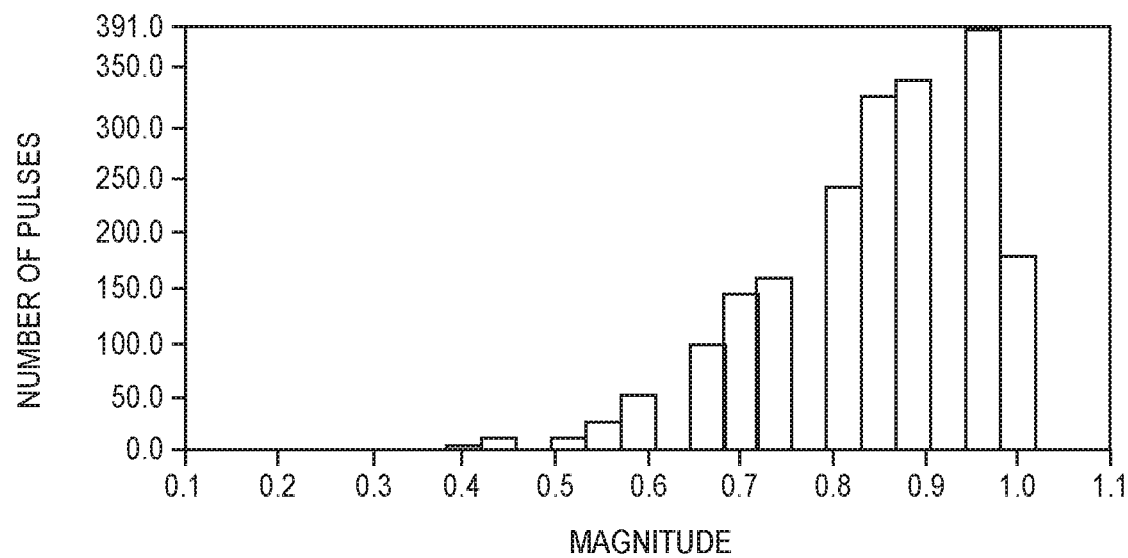
FIGS. 7A-7B are charts illustrating example values for a pulse current amplitude of electrical stimulation that varies over time based on a stochastic function in accordance with the techniques of the disclosure
Figure 7B:
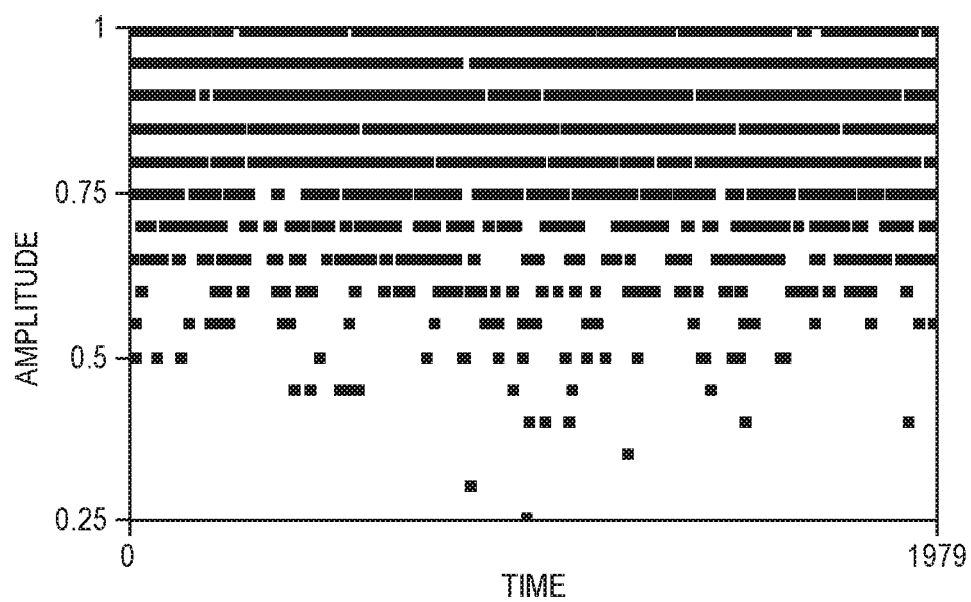

FIGS. 7A-7B are charts illustrating example values for a pulse current amplitude of electrical stimulation that varies over time based on a stochastic function in accordance with the techniques of the disclosure. In the example of FIGS. 7A-7B, IMD 102 delivers electrical stimulation therapy according to one or more parameters based on a stochastic function. In this example, IMD 102 delivers continuous electrical stimulation having a fixed frequency (e.g., of approximately 10 Hertz, a fixed pulse width (e.g., of approximately 210 microseconds), and an upper bound for a pulse current amplitude that is the maximum tolerable current amplitude, 7.8 milliamps, as described above. Further, IMD 102 applies a stochastic function to the pulse current amplitude of the electrical stimulation. In this example, the stochastic function defines a series of pseudo-random values for the pulse current amplitude according to a unimodal half-normal distribution having a one-sided coefficient of variation of 0.2 to 0.8 and a range of 0 to 7.8 milliamps. Hence, in this example, the frequency and pulse width are fixed but the pulse current amplitude varies based on the stochastic function.

FIG. 7A is a chart illustrating example values for a pulse current amplitude of electrical stimulation that varies over time based on a stochastic function. In the example of FIG. 7A, the stochastic function is a normalized probability density function. The x-axis of FIG. 7A indicates a magnitude of a value generated by the stochastic function. In this example, the x-axis is normalized such that 0 along the x-axis indicates 0 milliamps, while 1.0 along the x-axis indicates the maximum tolerable value of the amplitude of the electrical stimulation, such as 7.8 milliamps in one example. The y-axis of FIG. 7A depicts a count of electrical stimulation pulses for each magnitude of pulse current amplitude of the electrical stimulation. As illustrated by FIG. 7A, IMD 102 delivers electrical stimulation having a pulse current amplitude that varies over time based on the stochastic function.

FIG. 7B is a chart illustrating example values for the pulse current amplitude of electrical stimulation that varies over time based on the stochastic function of FIG. 7A as it is delivered to patient 112. The x-axis of FIG. 7B illustrates time, while the y-axis of FIG. 7B illustrates a magnitude of a value generated by the stochastic function. In this example, the y-axis is normalized such that 0 along the y-axis indicates 0 milliamps, while 1.0 along the y-axis indicates the maximum tolerable value of the amplitude of the electrical stimulation, 7.8 milliamps. As illustrated by FIG. 7B, IMD 102 delivers electrical stimulation having a pulse current amplitude that varies over time based on the stochastic function.

FIGS. 8A-8B are charts illustrating example values for a frequency of electrical stimulation that varies over time based on a stochastic function in accordance with the techniques of the disclosure. In the example of FIGS. 8A-8B, IMD 102 delivers electrical stimulation therapy according to one or more parameters based on a stochastic function. In this example, IMD 102 delivers continuous electrical stimulation having a fixed pulse width (e.g., of approximately 210 microseconds) and one of a fixed voltage or fixed current amplitude having a maximum tolerable value for the amplitude, as described above. Further, IMD 102 applies a stochastic function to the frequency of the electrical stimulation. In this example, the stochastic function defines a series of pseudo-random values for the frequency according to a unimodal Gaussian distribution having a median frequency of 10 Hertz, a coefficient of variation of ±0.2 to 0.8, and a range of 0.15 to 40 Hertz. In this case, frequency values of the stimulation may vary between 0.15 and 40 Hertz based on the stochastic function. Hence, in this example, the pulse amplitude and pulse width are fixed but the pulse rate, i.e., frequency, varies based on the stochastic function.

The duration of each stimulation cycle is a function of the pulse rate multiplied by the pulse width. In examples where at least one of the pulse rate, pulse width, or pulse duration vary over time based on the stochastic function, the duration of each stimulation cycle varies with the degree of randomness of the stochastic function. As an illustration of the above, in one example, stochastic lookup tables 215 include defined values for 990 separate electrical stimulation pulses. For system that varies the frequency of the electrical stimulation based on a stochastic function defining a normal probabilistic distribution centered at 10 Hertz and having 80% variability, the stimulation cycle duration is approximately 104 seconds before repeating, but varies each time due to the randomness of the frequency. The number of values stored within stochastic lookup tables 215 may be limited based on the amount of memory that stochastic lookup tables 215 and/or processing circuitry 210 possess. For example, other stochastic lookup tables 215 may include differing amounts of memory, and thus may be able to store greater or fewer values than the values for the 990 separate electrical stimulation pulses in the foregoing example, such as values for 500 separate electrical stimulation pulses or values for 1000 separate electrical stimulation pulses. The actual number of values for separate electrical stimulation pulses may be determined by the capacity of a storage medium that implements stochastic lookup tables 215.

Further, as described above, in some examples, IMD 102 does not include stochastic lookup tables 215. Rather, IMD 102 delivers electrical stimulation having one or more parameters that vary over time based on one or more values of a stochastic function that processing circuitry 210 generates in real-time.

FIG. 8A is a chart illustrating example values for a frequency of electrical stimulation that varies over time based on a stochastic function. The x-axis of FIG. 8A indicates values for the frequency of the electrical stimulation, as defined by the stochastic function. 10.0 along the x-axis indicates a mean of the frequency of the electrical stimulation, 10 Hertz. The y-axis of FIG. 8A depicts a count of inter-pulse periods wherein, for each inter-pulse period, the length of the inter-pulse period varies over time based on a frequency defined by the stochastic function. As illustrated by FIG. 8A, IMD 102 delivers electrical stimulation having a pulse frequency that varies over time based on the stochastic function.

FIG. 8B is a chart illustrating example values for the frequency of the electrical stimulation that varies over time based on the stochastic function of FIG. 8A as it is delivered to patient 112. The x-axis of FIG. 8B illustrates time, while the y-axis of FIG. 8B illustrates a pulse frequency of the electrical stimulation generated by the stochastic function. In this example, 10.0 along the y-axis indicates the mean frequency of the electrical stimulation, 10 Hertz. As illustrated by FIG. 8B, IMD 102 delivers electrical stimulation having a frequency that varies over time based on the stochastic function.

Figure 9:
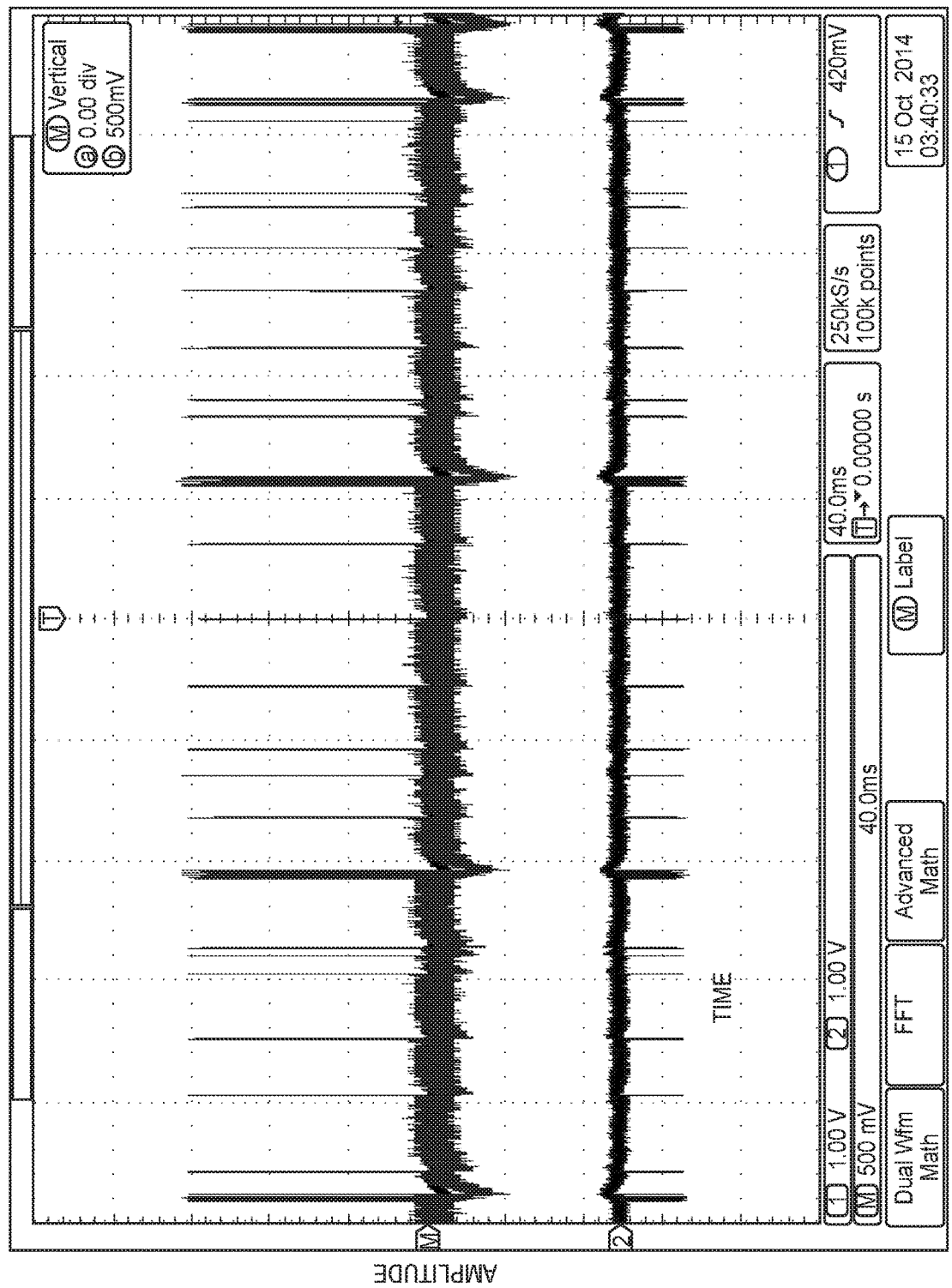
FIG. 9 is a chart illustrating example values for a pulse voltage amplitude of electrical stimulation that varies over time based on a stochastic function in accordance with the techniques of the disclosure.

FIG. 9 is a chart illustrating example values for a pulse voltage amplitude of electrical stimulation that varies over time based on a stochastic function in accordance with the techniques of the disclosure. Specifically, FIG. 9 depicts an oscilloscope screenshot of a pseudo-stochastic frequency stimulation pattern generated by IMD 102 in accordance with the techniques of the disclosure. The x-axis of FIG. 9 depicts time, while the y-axis of FIG. 9 depicts a pulse voltage of the electrical stimulation. Such pseudo-stochastic stimulation as depicted in FIG. 9 is based on a stochastic lookup table that contains 990 values for one or more parameters of the electrical stimulation so as to define 990 discrete stimulation events. In this example, IMD 102 delivers each of the 990 stimulation events sequentially and then repeats from the beginning of stochastic table 215. Thus, the duration of the pseudo-stochastic stimulation can vary depending upon the defined frequency of the electrical stimulation and coefficient of variation of the stochastic function.

In the example of FIG. 9, the stochastic lookup table contains 990 values for the one or more parameters of the electrical stimulation. However, the techniques of the disclosure may implement a stochastic lookup table that has more or less values for the one or more parameters of the electrical stimulation. For example, the number of values may be about 500, about 1000, or another number of values as dictated by the capacity of a storage medium that implements the stochastic lookup table.

Figure 10:
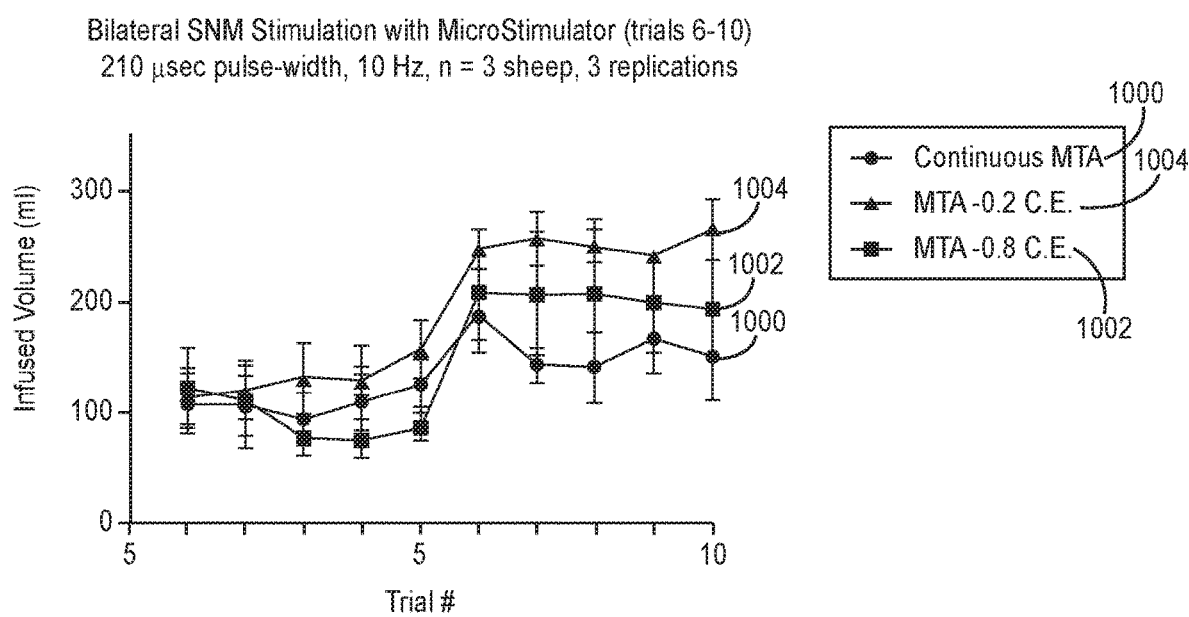
FIG. 10 is a chart illustrating example responses of sheep subjects receiving electrical stimulation having one or more parameters that vary over time based on a stochastic function, in accordance with the techniques of the disclosure.

FIG. 10 is a chart illustrating example responses of sheep subjects receiving electrical stimulation having one or more parameters that vary over time based on a stochastic function, in accordance with the techniques of the disclosure. In the example of FIG. 10, the x-axis depicts a particular experimental trial, while the y-axis depicts an average infused volume of a bladder of a sheep. The average infused volume indicates that amount of fluid that a sheep was able to retain prior to voiding. FIG. 10 illustrates that electrical stimulation having one or more parameters that vary over time based on a stochastic function, as described herein, may allow a subject to have greater bladder retention prior to voiding than electrical stimulation that has fixed parameters.

In the example of FIG. 10, an electrical stimulation device delivered, to 3 sheep, continuous electrical stimulation 1000 having a fixed frequency (e.g., of approximately 10 Hertz), a fixed pulse width (e.g., of approximately 210 microseconds), and a fixed pulse current amplitude having a magnitude that is a maximum tolerable value, determined as described above.

Further, the electrical stimulation device delivered, to 3 sheep, continuous electrical stimulation 1002 according to one or more parameters based on a stochastic function. Electrical stimulation 1002 had a fixed frequency (e.g., of approximately 10 Hertz), a fixed pulse width (e.g., of approximately 210 microseconds), and an upper bound for a pulse current amplitude having a magnitude that is a maximum tolerable value, determined as described above. Further, IMD 102 applied a stochastic function to the pulse current amplitude of the electrical stimulation. The stochastic function of continuous electrical stimulation 1002 defined a series of pseudo-random values for the pulse current amplitude according to a unimodal Gaussian distribution having a one-sided coefficient of variation of 0.8 and a range of 0 to the maximum tolerable value. Hence, in this example, the frequency and pulse width are fixed but the pulse current amplitude varies based on the stochastic function.

Further, the electrical stimulation device delivered, to 3 sheep, continuous electrical stimulation 1004 according to one or more parameters based on a stochastic function. Electrical stimulation 1004 had a fixed frequency (e.g., of approximately 10 Hertz), a fixed pulse width (e.g., of approximately 210 microseconds), and an upper bound for a pulse current amplitude having a magnitude that is the maximum tolerable value, determined as described above. Further, IMD 102 applied a stochastic function to the pulse current amplitude of the electrical stimulation. The stochastic function of continuous electrical stimulation 1002 defined a series of pseudo-random values for the pulse current amplitude according to a unimodal Gaussian distribution having a one-sided coefficient of variation of 0.8 and a range of 0 to the maximum tolerable value. Hence, in this example, the frequency and pulse width are fixed but the pulse current amplitude varies based on the stochastic function.

The example of FIG. 10 illustrates that sheep receiving electrical stimulation having a pulse current amplitude that varies over time based on a stochastic function may demonstrate a large bladder quieting response that allows for greater retained volumes of fluid prior to voiding. The bladder quieting response to stochastic pulse current amplitude stimulation may be larger than that induced by constant stimulation with fixed pulse current amplitudes. Such greater bladder quieting response likely results from a richer or larger information-carrying capacity of the input signal or by activating richer or larger information transmission capacities within targeted nerves. Thus, such electrical stimulation as described herein may exhibit greater efficacy than conventional electrical stimulation therapies.

FIGS. 11A-11E are charts illustrating example values for the one or more parameters of the electrical stimulation that vary over time based on a stochastic function, in accordance with the techniques of the disclosure. The x-axis of FIGS. 11A-11E depict an amplitude of the electrical stimulation, while the y-axis depicts a number of electrical stimulation pulses delivered for that corresponding amplitude of the electrical stimulation. The response of nerve fibers of patient 112 to the electrical stimulation may vary depending on the distance and orientation of the nerve fibers to the electrical stimulation. In other words, the nerve fiber response may be location-dependent (e.g., depend on whether the nerve fibers receive near-field or far-field electrical stimulation). Such variation of the one or more parameter values of the electrical stimulation over time may deliver near-field or far-field electrical stimulation to the nerve fibers, evoking varying responses from the nerve fibers over time. Thus, an amount of energy delivered to a target tissue versus an amount of energy that disperses into surrounding tissue may depend on the shape of the stochastic function that defines values for the one or more parameters of the electrical stimulation that varies over time.

Figure 11A:
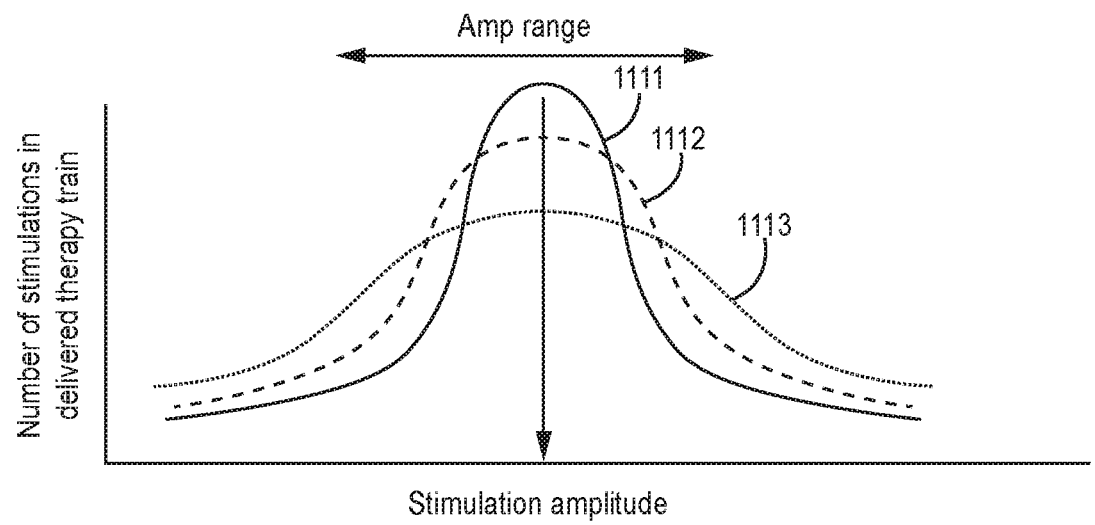
FIGS. 11A-11E are charts illustrating example values for the one or more parameters of the electrical stimulation that vary over time based on a stochastic function, in accordance with the techniques of the disclosure.

FIG. 11A depicts a family of distributions 1111, 1112, and 1113 of values for the one or more parameters, wherein the family of distributions have varying levels of distribution (e.g. different variance levels or distribution densities). Each electrical stimulation pulse train delivered according to each of distributions 1111, 1112, and 1113 may have the same energy delivered and the same maximum stimulation amplitude. However, the distributions of amplitudes delivered to patient 112 are different for each electrical stimulation pulse train (e.g., each of distributions 1111, 1112, and 1113 has increasing variability).

Figure 11B:
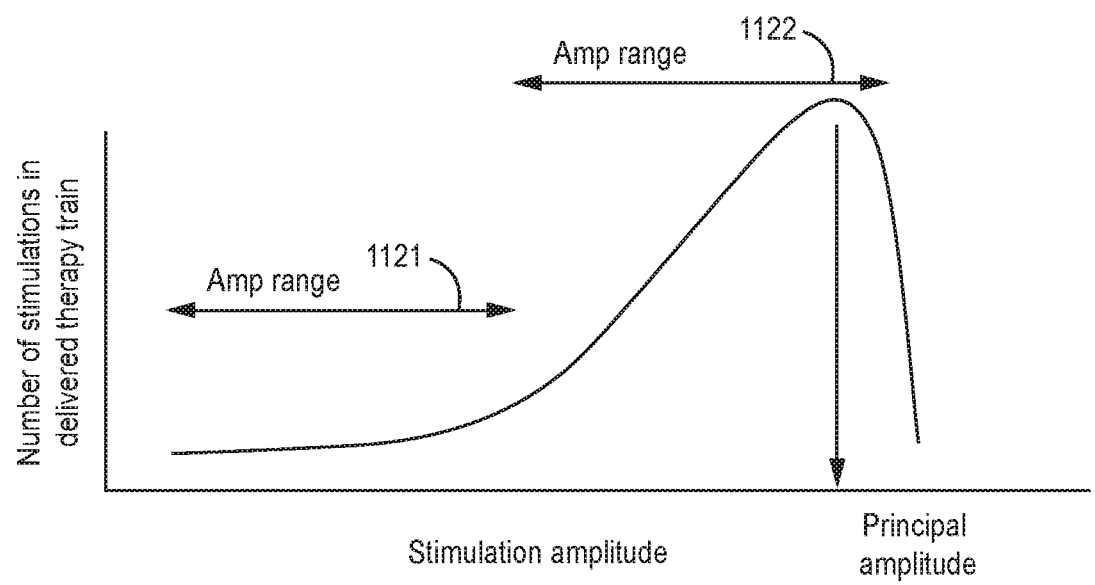

FIG. 11B depicts a probabilistic distribution for an electrical stimulation pulse train having therapy amplitude pulses that vary around a skewed principal amplitude. In some examples, electrical stimulation pulses 1121 having a lower amplitude may act on nerve fibers closer to the contacts of electrodes 114A-1114D and 115A-115D of leads 116. In contrast, electrical stimulation pulses 1122 having a higher amplitude may activate or impact fibers at a greater distance from the contacts of electrodes 114A-1114D and 115A-115D, as well as those nerve fibers close to the contacts of electrodes 114A-1114D and 115A-115D. Depending on the amplitude of the electrical stimulation and the proximity of the nerve fibers to electrodes 114A-1114D and 115A-115D, a nerve fiber close to electrodes 114A-1114D and 115A-115D receiving electrical stimulation having a particular magnitude may be inhibited, while a nerve fiber more distant to electrodes 114A-1114D and 115A-115D may be stimulated by the same electrical stimulation.

Figure 11C:
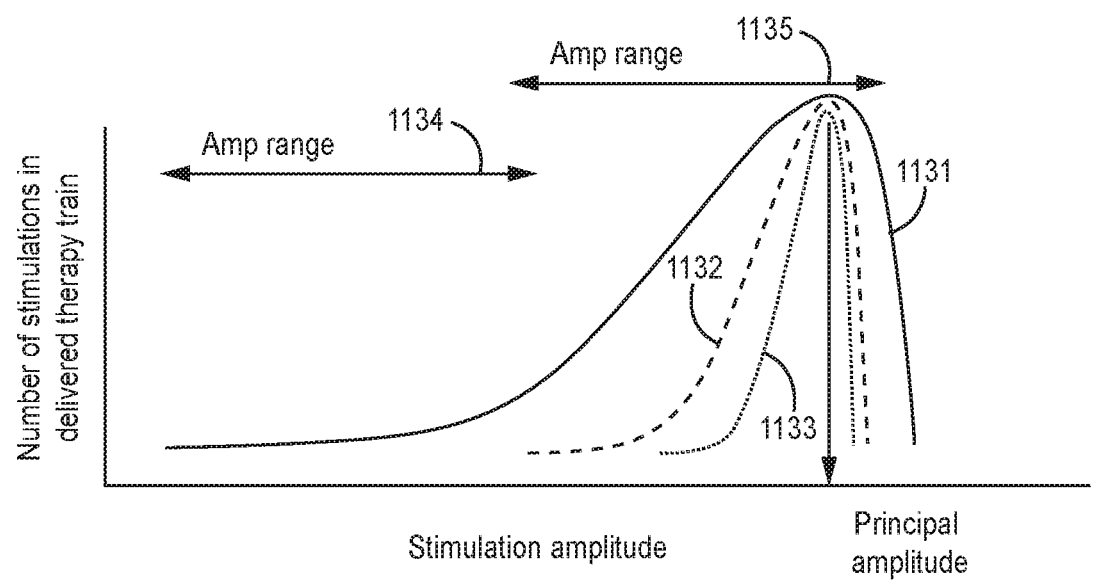

FIG. 11C depicts probabilistic distributions for an electrical stimulation pulse train having therapy amplitude pulses varied around a skewed principal amplitude. Electrical stimulation pulses 1134 having a lower amplitude may act on nerve fibers closer to electrodes 114A-1114D and 115A-115D. In some examples, the electrical stimulation pulses 1134 may cause no activation or minimal activation. Electrical stimulation pulses 1135 having a higher amplitude may activate or impact fibers at a greater distance from the contacts of electrodes 114A-1114D and 115A-115D, as well as those nerve fibers close to the contacts of electrodes 114A-1114D and 115A-115D. Each of probabilistic distributions 1131, 1132, and 1133 represent stochastic functions having identical principal amplitudes but different variabilities of electrical stimulation. Probabilistic distributions 1133 represents an electrical stimulation pulse train with low variance, probabilistic distributions 1132 represents an electrical stimulation pulse train with medium variance, and probabilistic distributions 1131 represents an electrical stimulation pulse train with a high variance.

Figure 11D:
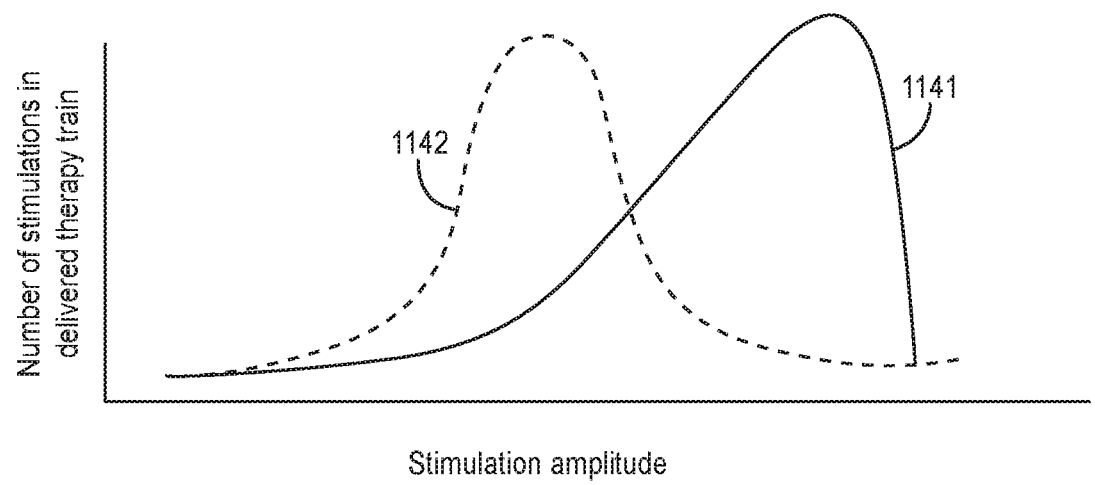

FIG. 11D depicts probabilistic distribution for electrical stimulation pulse trains. Probabilistic distribution 1142 represents electrical stimulation pulses having an amplitude that varies around a centered principal amplitude, such as for a normal or Gaussian probabilistic distribution). Probabilistic distribution 1141 represents electrical stimulation pulses having an amplitude that varies around a skewed center amplitude. Electrical stimulation pulses having a lower amplitude may act on nerve fibers closer to electrodes 114A-1114D and 115A-115D. In contrast, electrical stimulation pulses having a higher amplitude may activate or impact fibers at a greater distance from the contacts of electrodes 114A-1114D and 115A-115D, as well as those nerve fibers close to the contacts of electrodes 114A-1114D and 115A-115D.

Figure 11E:
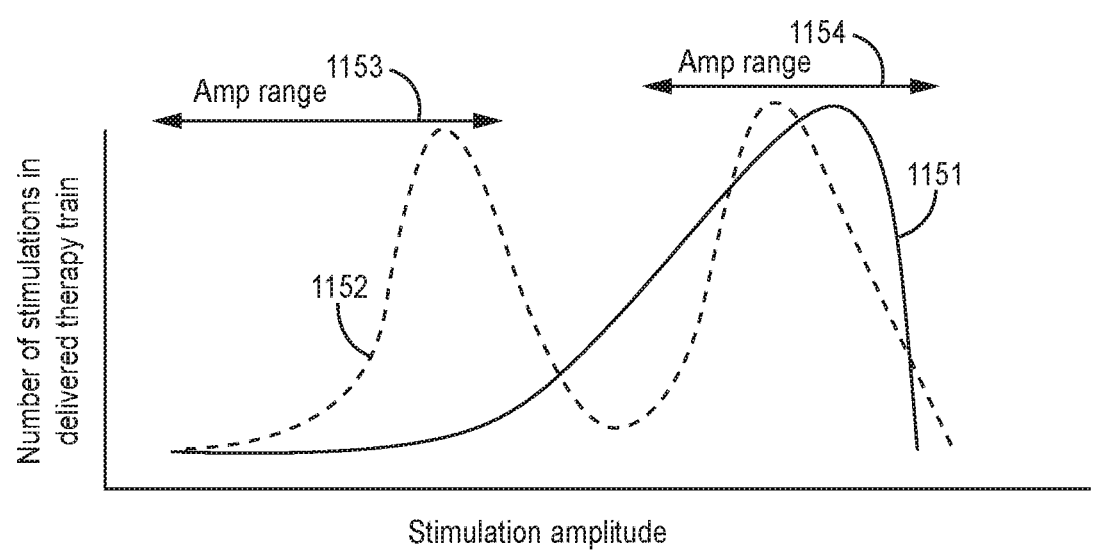

FIG. 11E depicts probabilistic distribution for electrical stimulation pulse trains. Probabilistic distribution 1152 represents electrical stimulation pulses varied around two center amplitudes (e.g., a bimodal probabilistic distribution). In one example, electrical stimulation pulses 1153 of probabilistic distribution 1152 having a lower amplitude and electrical stimulation pulses 1154 of probabilistic distribution 1152 having a higher amplitude have the same electrical stimulation frequency. In other examples, electrical stimulation pulses 1153 of probabilistic distribution 1152 having a lower amplitude and electrical stimulation pulses 1154 of probabilistic distribution 1152 having a higher amplitude have different electrical stimulation frequencies. For example, a low amplitude may stimulate target sites closer to electrodes 114A-1114D and 115A-115D, while a high amplitude may stimulate target sites farther from to electrodes 114A-1114D and 115A-115D as well as target sites closer to electrodes 114A-1114D and 115A-115D. Similarly, a low frequency may stimulate target sites closer to electrodes 114A-1114D and 115A-115D, while a high frequency may stimulate target sites farther from to electrodes 114A-1114D and 115A-115D as well as target sites closer to electrodes 114A-1114D and 115A-115D.

Probabilistic distribution 1151 represents electrical stimulation pulses varied around a skewed center amplitude. In some examples, electrical stimulation pulses 1153 of probabilistic distribution 1151 having a lower amplitude may act on nerve fibers closer to the contacts of electrodes 114A-1114D and 115A-115D of leads 116. In contrast, electrical stimulation pulses 1154 of probabilistic distribution 1151 having a higher amplitude may activate or impact fibers at a greater distance from the contacts of electrodes 114A-1114D and 115A-115D, as well as those nerve fibers close to the contacts of electrodes 114A-1114D and 115A-115D.

Figure 12:
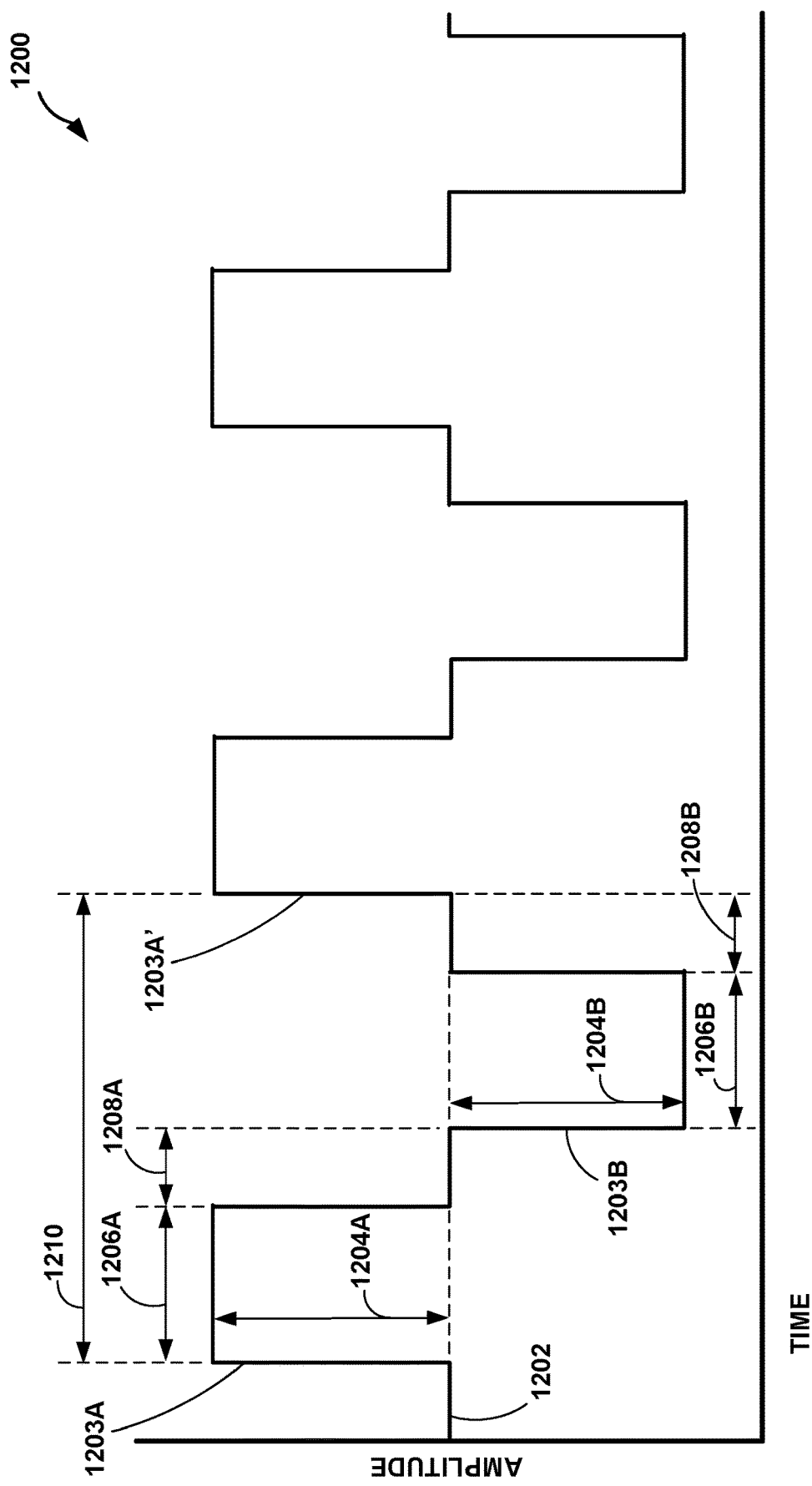
FIG. 12 is a diagram illustrating example parameters of electrical stimulation that the example system of FIG. 1 may modify by introducing complex variation, in accordance with the techniques of the disclosure.

FIG. 12 is a diagram 1200 illustrating example parameters of electrical stimulation that the example system 100 of FIG. 1 may modify by introducing complex variation, in accordance with the techniques of the disclosure. FIG. 12 is described with respect to FIGS. 1 and 2 for convenience.

In the example of FIG. 12, IMD 102 delivers electrical stimulation therapy 1202 comprising electrical stimulation therapy pulse 1203A and recharge pulse 1203B. As discussed above, IMD 102 may modify one or more electrical stimulation parameters of electrical stimulation therapy 1202 by introducing complex variation to the one or more electrical stimulation parameters. For example, the complex variation may be based on a periodic or stochastic function. In the example of FIG. 12, IMD 102 uses a stochastic function to determine a series of values for one or more parameters of electrical stimulation therapy 1202, such as combination of electrodes 114 of FIG. 2, a polarity of electrodes 114, amplitude 1204A of electrical stimulation therapy pulse 1203A, amplitude 1204B of recharge pulse 1203B, pulse width 1206A of electrical stimulation therapy pulse 1203A, pulse width 1206B of recharge pulse 1203B, recharge interval 1208A, inter-stimulation interval 1208B, pulse rate or pulse frequency 1210, a duty cycle of electrical stimulation therapy pulse 1203A (e.g., a ratio of pulse width 1206A to inter-stimulation interval 1208B) and/or a duty cycle of recharge pulse 1203B (e.g., a ratio of pulse width 1206B to recharge interval 1208A). IMD 102 may generate electrical stimulation defined by complex variation of the one or more electrical stimulation parameters by using the series of values determined with the stochastic function as values for the one or more electrical stimulation parameters defining the electrical stimulation.

As depicted in the example of FIG. 12, recharge interval 1208A depicts an interval of time between electrical stimulation therapy pulse 1203A and recharge pulse 1203B, wherein, during recharge interval 1208A, no electrical stimulation is delivered. Inter-stimulation interval 1208B depicts a time between each period of electrical stimulation therapy 1202 (e.g., one electrical stimulation therapy pulse 1203A and one recharge pulse 1203B), wherein, during inter-stimulation interval 1208B, no electrical stimulation is delivered. In examples where each period of electrical stimulation therapy 1202 comprises one electrical stimulation therapy pulse 1203A and one recharge pulse 1203B, such as is depicted in the example of FIG. 12, inter-stimulation interval 1208B depicts an interval of time between recharge pulse 1203B and a subsequent electrical stimulation therapy pulse 1203A' during which no electrical stimulation is delivered. In examples where each period of electrical stimulation therapy 1202 comprises only electrical stimulation therapy pulses 1203A (e.g., and no recharge pulses), inter-stimulation interval 1208B depicts an interval of time between recharge pulse 1203B and a subsequent electrical stimulation therapy pulse 1203A'.

In some examples, IMD 102 uses a different stochastic function determine a different series of values for each of the one or more parameters of electrical stimulation therapy 1202. In other examples, IMD 102 uses the same stochastic function determine a series of values for each of the one or more parameters of electrical stimulation therapy 1202. In some examples, instead of or in addition to using the stochastic function, IMD 102 uses a periodic function to determine the series of values for each of the one or more parameters of electrical stimulation therapy 1202.

In one example, pulse amplitudes 1204A and 1204B are pulse current amplitudes. In some examples, electrical stimulation therapy 1202 has pulse current amplitudes 1204A and 1204B selected from a range of 0 milliamps to 40 milliamps. In other examples, electrical stimulation therapy 1202 has pulse current amplitudes 1204A and 1204B selected from a range of 0 milliamps to 25 milliamps. In other examples, electrical stimulation therapy 1202 has pulse current amplitudes 1204A and 1204B selected from a range of 0.1 milliamps to 25 milliamps. In other examples, electrical stimulation therapy 1202 has pulse current amplitudes 1204A and 1204B selected from a range of 0 milliamps to 7.8 milliamps.

In some examples, IMD 102 delivers continuous electrical stimulation having a frequency 1210 of about 10 Hertz, pulse widths 1206A and 1206B of about 210 microseconds, and an upper bound for a pulse current amplitudes 1204A and 1204B that is the maximum tolerable current amplitude, as described above. Further, IMD 102 applies a stochastic function to pulse current amplitudes 1204A and 1204B of electrical stimulation therapy 1202. In this example, the stochastic function defines a series of pseudo-random values for pulse current amplitudes 1204A and 1204B according to a unimodal Gaussian distribution having a one-sided coefficient of variation of 0.2 to 0.8 and a range of 0 to 7.8 milliamps. In some examples, amplitude 1204A of electrical stimulation therapy pulse 1203A is about the same as amplitude 1204B of recharge pulse 1203B. In other examples, amplitude 1204A of electrical stimulation therapy pulse 1203A is greater than or less than amplitude 1204B of recharge pulse 1203B.

In some examples, amplitudes 1204A and 1204B are current amplitudes selected from a range of 0 milliamps to 40 milliamps. In other examples, amplitudes 1204A and 1204B are current amplitudes selected from a range of 0 milliamps to 25 milliamps. In other examples, amplitudes 1204A and 1204B are current amplitudes selected from a range of 0.1 milliamps to 25 milliamps. In other examples, amplitudes 1204A and 1204B are current amplitudes selected from a range of 0 milliamps to 7.8 milliamps. In some examples, amplitudes 1204A and 1204B are voltage amplitudes selected from a range of 50 millivolts to 10 volts. In another example, amplitudes 1204A and 1204B are voltage amplitudes selected from a range of 500 millivolts to 5 volts.

In some examples, one or more electrical stimulation parameters of electrical stimulation 1202 are selected with respect to the maximum tolerable value, as determined above. For example, one or more electrical stimulation parameters of electrical stimulation 1202 may be selected as a percentage of the maximum tolerable value. In one example, one or more electrical stimulation parameters of electrical stimulation 1202 are selected from a range of values between about 5% to about 80% of the maximum tolerable value. In some examples, values for one or more of amplitude 1204A, amplitude 1204B, pulse width 1206A, pulse width 1206B, recharge interval 1208A, inter-stimulation interval 1208B, pulse rate or pulse frequency 1210, a duty cycle of electrical stimulation therapy pulse 1203A and/or a duty cycle of recharge pulse 1203B may be selected as a percentage of the maximum tolerable value.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuitry, modules or components may be implemented together or separately as discrete but interoperable logic devices. Depiction of different features as circuitry, modules, or units is intended to highlight different functional aspects and does not necessarily imply that such circuitry, modules, or units must be realized by separate hardware or software components. Rather, functionality associated with one or more circuits, modules, or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method for providing neuromodulation therapy to a patient using an implantable medical device (IMD), the method comprising:
    obtaining, with processing circuitry of the IMD, values of a plurality of electrical stimulation parameters for at least one pulse train of electrical stimulation, the plurality of electrical stimulation parameters including a value of a pulse amplitude;
    defining, with the processing circuitry of the IMD and to reduce a pelvic symptom of the patient, a variation to the value of the pulse amplitude, the variation comprising a series of variations of a value of the pulse amplitude, wherein a quantity of variations of the value of the pulse amplitude in the series of variations of the value of the pulse amplitude is selected to reduce the pelvic symptom of the patient, wherein the quantity of variations is greater than or equal to 500, and wherein a coefficient of variation of the series of variations is from 0.2 to 0.8;
    obtaining, with the processing circuitry of the IMD, a maximum patient specific value for the pulse amplitude;
    modifying, with the processing circuitry of the IMD, values of the pulse amplitude of pulses of the at least one pulse train of electrical stimulation, wherein modifying the values of the pulse amplitude comprises setting values of pulse amplitudes of the pulses of the at least one pulse train of electrical stimulation to pulse amplitudes of the series of variations, wherein modifying the at least one pulse train of electrical stimulation comprises setting values of pulse amplitudes of the pulses of the at least one pulse train to be less than or equal to the maximum patient specific value, and wherein an amount of energy used to deliver the modified at least one pulse train of electrical stimulation is less than or equal an amount of energy that would be used to deliver the at least one pulse train of electrical stimulation; and
    generating, with a stimulation generator of the IMD, the modified at least one pulse train of electrical stimulation.

2. The method of claim 1, further comprising controlling, with the processing circuitry of the IMD, delivery of the modified at least one pulse train of electrical stimulation to the patient via implantable electrodes to reduce the pelvic symptom of the patient.

3. The method of claim 1, wherein the pulse amplitude comprises one of a pulse voltage amplitude or a pulse current amplitude of the electrical stimulation.

4. The method of claim 1, wherein the plurality of electrical stimulation parameters further includes a pulse width of the electrical stimulation, and wherein the method further comprises:
    defining, with the processing circuitry of the IMD and to reduce the pelvic symptom of the patient, a variation to the pulse width, the variation comprising a series of variations of a value of the pulse width, wherein a quantity of variations of the value of the pulse width in the series of variations of the value of the pulse width is selected to reduce the pelvic symptom of the patient; and
    modifying, with the processing circuitry of the IMD, values of the pulse width of the pulses of the at least one pulse train of electrical stimulation, wherein modifying the values of the pulse width comprises setting values of pulse widths of the pulses of the at least one pulse train of electrical stimulation to pulse widths of the series of variations of the value of the pulse width.

5. The method of claim 1, wherein the plurality of electrical stimulation parameters further includes a duty cycle of the electrical stimulation, and wherein the method further comprises:
    defining, with the processing circuitry of the IMD and to reduce the pelvic symptom of the patient, a variation to the duty cycle, the variation comprising a series of variations of a value of the duty cycle, wherein a quantity of variations of the value of the duty cycle of the electrical stimulation is selected to reduce the pelvic symptom of the patient; and
    modifying, with the processing circuitry of the IMD, values of the duty cycle of the at least one pulse train of electrical stimulation to values of the series of variations of the value of the duty cycle.

6. The method of claim 1, wherein the plurality of electrical stimulation parameters further includes a pulse frequency of the electrical stimulation, and wherein the method further comprises:
- defining, with the processing circuitry of the IMD and to reduce the pelvic symptom of the patient, a variation to the pulse frequency, the variation comprising a series of variations of a value of the pulse frequency, wherein a quantity of variations of the value of the pulse frequency in the series of variations of the value of the pulse frequency is selected to reduce the pelvic symptom of the patient; and
- modifying, with the processing circuitry of the IMD, values of the pulse frequency of pulses of the at least one pulse train of electrical stimulation, wherein modifying the values of the pulse frequency comprises setting values of pulse frequencies of the pulses of the at least one pulse train of electrical stimulation to pulse frequencies of the series of variations of the value of the pulse frequency.

7. The method of claim 1, wherein the at least one pulse train of electrical stimulation comprises stimulation pulses interleaved with recharge pulses, and the plurality of electrical stimulation parameters further includes a recharge interval between the stimulation pulses and the recharge pulses of the at least one pulse train of electrical stimulation, and wherein the method further comprises:
- defining, with the processing circuitry of the IMD and to reduce the pelvic symptom of the patient, a variation to the recharge interval, the variation comprising a series of variations of a value of the recharge interval, wherein a quantity of variations of the value of the recharge interval in the series of variations of the value of the recharge interval is selected to reduce the pelvic symptom of the patient; and
- modifying, with the processing circuitry of the IMD, values of the recharge interval of the at least one pulse train of electrical stimulation to values of the series of variations of the value of the recharge interval.

8. The method of claim 1, wherein the plurality of electrical stimulation parameters further includes an inter-stimulation interval between each stimulation pulse of the at least one pulse train of electrical stimulation, and wherein the method further comprises:
- defining, with the processing circuitry of the IMD and to reduce the pelvic symptom of the patient, a variation to the inter-stimulation interval, the variation comprising a series of variations of a value of the inter-stimulation interval, wherein a quantity of variations of the value of the inter-stimulation interval in the series of variations of the value of the inter-stimulation interval is selected to reduce the pelvic symptom of the patient; and
- modifying, with the processing circuitry of the IMD, values of the inter-stimulation interval of the at least one pulse train of electrical stimulation to values of the series of variations of the value of the inter-stimulation interval.

9. The method of claim 1, wherein the pulse amplitude comprises one of a pulse voltage amplitude or a pulse current amplitude of the electrical stimulation, and the maximum patient specific value is a maximum tolerable value of the patient for the one of the pulse voltage amplitude or the pulse current amplitude.

10. The method of claim 1, wherein the variation to the value of the pulse amplitude comprises a stochastic variation to the value of the pulse amplitude, and wherein the stochastic variation defines a distribution of values based on one of:
- a unimodal Gaussian distribution; or
- a multimodal Gaussian distribution.

11. The method of claim 10, wherein the stochastic variation to the value of the pulse amplitude comprises values for the pulse amplitude that are within one standard deviation of a mean value of the distribution of values.

12. The method of claim 10, wherein the stochastic variation to the value of the pulse amplitude comprises values for the pulse amplitude that are within two standard deviations of a mean value of the distribution of values.

13. The method of claim 10,
- wherein modifying the at least one pulse train of electrical stimulation comprises modifying pulse amplitudes of the pulses with repetitions of the series of variations, and
- wherein the method further comprises controlling, with the processing circuitry of the IMD, delivery of the at least one pulse train of electrical stimulation to the patient via implantable electrodes.

14. The method of claim 1, wherein the pelvic symptom is one or more of:
- over-active bladder;
- urinary incontinence;
- fecal incontinence;
- sexual dysfunction; or
- pelvic pain.

15. The method of claim 1, wherein defining the variation further comprises:
- generating, based on a stochastic function, the series of variations of the value of the pulse amplitude as including greater than or equal to 500 different values of the pulse amplitude.

16. The method of claim 15, further comprising:
- storing, in a lookup table, the different values of the pulse amplitude,
- wherein setting values of pulse amplitudes of the pulses comprises:
  - responsive to determining that an ith value of the pulse amplitude in the lookup table is not less than the maximum patient specific value, setting the ith value of the pulse amplitude to the maximum patient specific value.

17. The method of claim 1, wherein the quantity of variations of the value of the pulse amplitude in the series of variations of the value of the pulse amplitude is further selected based on one or more parameters of the IMD.

18. The method of claim 1, wherein obtaining, with the processing circuitry of the IMD, the values of the plurality of electrical stimulation parameters comprises:
- receiving, via telemetry circuitry of the IMD and from a programmer device, the value of the pulse amplitude.

19. An implantable medical device (IMD) configured to provide neuromodulation therapy to a patient comprising:
- a stimulation generator configured to generate at least one pulse train of electrical stimulation for delivery to the patient; and
- processing circuitry configured to:
  - obtain values of a plurality of electrical stimulation parameters for the at least one pulse train of electrical stimulation, the plurality of electrical stimulation parameters including a value of a pulse amplitude;
  - define, to reduce a pelvic symptom of the patient, a variation to the value of the pulse amplitude, the variation comprising a series of variations of a value of the pulse amplitude, wherein a quantity of variations of the value of the pulse amplitude in the series of variations of the value of the pulse amplitude is selected to reduce the pelvic symptom of the patient, wherein the quantity of variations is greater than or equal to 500, and wherein a coefficient of variation of the series of variations is from 0.2 to 0.8;

obtain a maximum patient specific value for the pulse amplitude;

modify values of the pulse amplitude of pulses of the at least one pulse train of electrical stimulation, wherein modifying the values of the pulse amplitude comprises setting values of pulse amplitudes of the pulses of the at least one pulse train of electrical stimulation to pulse amplitudes of the series of variations, wherein, to modify the values of the pulse amplitude of the pulses of the at least one pulse train of electrical stimulation, the processing circuitry is configured to set values of the pulse amplitudes of the pulses of the at least one pulse train to be less than or equal to the maximum patient specific value, and wherein an amount of energy used to deliver the modified at least one pulse train of electrical stimulation is less than or equal an amount of energy that would be used to deliver the at least one pulse train of electrical stimulation; and control the stimulation generator to generate the modified at least one pulse train of electrical stimulation.

20. The medical device of claim 19, wherein the variation to the value of the pulse amplitude comprises a stochastic variation to the value of the pulse amplitude, and wherein the stochastic variation defines a distribution of values based on one of:
a unimodal Gaussian distribution; or
a multimodal Gaussian distribution.

21. The medical device of claim 20, wherein the stochastic variation to the value of the pulse amplitude comprises values for the pulse amplitude that are within one standard deviation of a mean value of the distribution of values.

22. The medical device of claim 19, wherein the pelvic symptom is one or more of:
over-active bladder;
urinary incontinence;
fecal incontinence;
sexual dysfunction; or
pelvic pain.

23. An implantable medical device configured to provide neuromodulation therapy to a patient comprising:

means for obtaining values of a plurality of electrical stimulation parameters for at least one pulse train of electrical stimulation, the plurality of electrical stimulation parameters including a value of a pulse amplitude;

means for defining, to reduce a pelvic symptom of the patient, a variation to the value of the pulse amplitude, the variation comprising a series of variations of a value of the pulse amplitude, wherein a quantity of variations of the value of the pulse amplitude in the series of variations of the value of the pulse amplitude is selected to reduce the pelvic symptom of the patient, wherein the quantity of variations is greater than or equal to 500, and wherein a coefficient of variation of the series of variations is from 0.2 to 0.8;

means for obtaining a maximum patient specific value for the pulse amplitude;

means for modifying values of the pulse amplitude of pulses of the at least one pulse train of electrical stimulation, wherein modifying the values of the pulse amplitude comprises setting values of pulse amplitudes of the pulses of the at least one pulse train of electrical stimulation to pulse amplitudes of the series of variations, wherein the means for modifying comprise means for setting values of pulse amplitudes of the pulses of the at least one pulse train to be less than or equal to the maximum patient specific value, and wherein an amount of energy used to deliver the modified at least one pulse train of electrical stimulation is less than or equal an amount of energy that would be used to deliver the at least one pulse train of electrical stimulation; and means for generating, the modified at least one pulse train of electrical stimulation.

24. A non-transitory, computer-readable medium comprising instructions that, when executed, cause processing circuitry of an implantable medical device (IMD) configured to provide neuromodulation therapy to a patient to:

obtain values of a plurality of electrical stimulation parameters for the at least one pulse train of electrical stimulation, the plurality of electrical stimulation parameters including a value of a pulse amplitude;

define, to reduce a pelvic symptom of the patient, a variation to the value of the pulse amplitude, the variation comprising a series of variations of a value of the pulse amplitude, wherein a quantity of variations of the value of the pulse amplitude in the series of variations of the value of the pulse amplitude is selected to reduce the pelvic symptom of the patient, wherein the quantity of variations is greater than or equal to 500, and wherein a coefficient of variation of the series of variations is from 0.2 to 0.8;

obtain a maximum patient specific value for the pulse amplitude;

modify values of the pulse amplitude of pulses of the at least one pulse train of electrical stimulation, wherein modifying the values of the pulse amplitude comprises setting values of pulse amplitudes of the pulses of the at least one pulse train of electrical stimulation to pulse amplitudes of the series of variations, wherein the instructions that cause the processing circuitry to modify comprise instructions that cause the processing circuitry to set values of pulse amplitudes of the pulses of the at least one pulse train to be less than or equal to the maximum patient specific value, and wherein an amount of energy used to deliver the modified at least one pulse train of electrical stimulation is less than or equal an amount of energy that would be used to deliver the at least one pulse train of electrical stimulation; and control a stimulation generator of the IMD to generate, as modified, the at least one pulse train of electrical stimulation.

* * * * *